US008778369B2

(12) United States Patent
Ahmed et al.

(10) Patent No.: US 8,778,369 B2
(45) Date of Patent: Jul. 15, 2014

(54) BARRIER FILM-FORMING COMPOSITIONS AND METHODS OF USE

(75) Inventors: Fahim U. Ahmed, Greensboro, NC (US); N. Camelia Traistaru, Kansas City, KS (US)

(73) Assignee: DeLaval Holding AB, Tumba (SE)

(*) Notice: Subject to any disclaimer, the term of this patent is extended or adjusted under 35 U.S.C. 154(b) by 367 days.

(21) Appl. No.: 12/471,190

(22) Filed: May 22, 2009

(65) Prior Publication Data

US 2009/0247485 A1 Oct. 1, 2009

Related U.S. Application Data

(63) Continuation-in-part of application No. 11/192,571, filed on Jul. 29, 2005, now abandoned, and a continuation-in-part of application No. 11/439,941, filed on May 24, 2006, now Pat. No. 8,153,613.

(51) Int. Cl.
*A01N 25/00* (2006.01)
*A61K 47/36* (2006.01)

(52) U.S. Cl.
USPC .......................... 424/405; 424/401; 424/488

(58) Field of Classification Search
USPC .......................................... 424/405; 536/123
See application file for complete search history.

(56) References Cited

U.S. PATENT DOCUMENTS

| | | | |
|---|---|---|---|
| 2,739,922 A | 3/1956 | Shelanski | |
| 3,972,997 A * | 8/1976 | Nakashio et al. | 514/54 |
| 3,993,777 A | 11/1976 | Caughman et al. | |
| 4,199,602 A | 4/1980 | Lentsch | |
| 4,434,181 A | 2/1984 | Marks, Sr. et al. | |
| 4,647,458 A | 3/1987 | Ueno et al. | |
| 4,695,453 A | 9/1987 | Tuominen et al. | |
| 4,844,898 A * | 7/1989 | Komori et al. | 424/672 |
| 4,945,110 A | 7/1990 | Brokken et al. | |
| 4,948,784 A * | 8/1990 | Mori et al. | 514/54 |
| 5,043,357 A | 8/1991 | Hoffler | |
| 5,063,249 A | 11/1991 | Andrews | |
| 5,139,771 A | 8/1992 | Gerstein | |
| 5,180,749 A | 1/1993 | Cusack et al. | |
| 5,225,096 A | 7/1993 | Ahmed et al. | |
| 5,518,902 A * | 5/1996 | Ozaki et al. | 435/102 |
| 5,735,812 A * | 4/1998 | Hardy | 602/43 |
| 5,776,479 A | 7/1998 | Pallos et al. | |
| 6,010,899 A * | 1/2000 | Thorne et al. | 435/254.1 |
| 6,030,633 A | 2/2000 | Hemling et al. | |
| 6,034,133 A | 3/2000 | Hendley et al. | |
| 6,102,205 A * | 8/2000 | Greff et al. | 206/438 |
| 6,329,343 B1 * | 12/2001 | Leung et al. | 514/23 |
| 6,582,734 B1 * | 6/2003 | Wei et al. | 424/665 |
| 6,727,228 B2 | 4/2004 | Janssen et al. | |
| 6,759,382 B2 | 7/2004 | Ahmed | |
| 6,878,378 B1 * | 4/2005 | Yamaki et al. | 424/401 |
| 7,402,323 B2 * | 7/2008 | Kligerman et al. | 424/678 |
| 7,994,141 B2 * | 8/2011 | Park et al. | 514/34 |
| 2003/0180377 A1 | 9/2003 | Ramirez et al. | |
| 2004/0241099 A1 | 12/2004 | Popp et al. | |
| 2005/0058719 A1 | 3/2005 | Ramirez et al. | |
| 2005/0255172 A1 | 11/2005 | Omidbakhsh | |
| 2006/0228319 A1 * | 10/2006 | Vona et al. | 424/70.13 |
| 2007/0077235 A1 | 4/2007 | Loomis et al. | |

FOREIGN PATENT DOCUMENTS

| | | |
|---|---|---|
| DE | 29514293 U1 | 1/1996 |
| DE | 19612057 A1 | 10/1997 |
| DE | 19627498 | 1/1998 |
| DE | 29900687 U1 | 4/1999 |
| DE | 19850994 A1 | 5/2000 |
| EP | 0505763 A1 | 9/1929 |
| EP | 0168243 A2 | 1/1986 |
| EP | 0251303 A2 | 1/1988 |
| EP | 0414309 A1 | 2/1991 |
| EP | 0640285 A1 | 3/1995 |
| EP | 896521 B1 | 11/1997 |
| EP | 1036511 A2 | 9/2000 |
| EP | 1080714 | 5/2007 |
| GB | 2393967 A | 4/2004 |
| WO | WO 92/09260 A1 | 6/1992 |
| WO | WO 96/11572 A1 | 4/1996 |
| WO | WO 96/29867 A2 | 10/1996 |
| WO | WO99/52360 | 10/1999 |
| WO | WO 00/13507 A1 | 3/2000 |
| WO | WO 00/16616 A1 | 3/2000 |

(Continued)

OTHER PUBLICATIONS

Database Biosis, Hartmann, A.A., et al; "Antibacterial Efficacy of an Anion-Active Detergent 6 vol. Percent Isopropanol and Salicyclic Acid and-or Phenol-Containing Isopropanol in Single and Combined Therapeutic Use" Abstract, Database Biosis; Zentralblatt für Bakteriologie, Mikrobiologie und Hygiene, vol. 186 No. 5-6; 1988; 1 page.

Database Biosis, Hartmann, A.A., et al; "Effect of the Application of an Anionic Detergent Combined With Fabry's Tincture and It's Components on Human Skin Resident Flroa Part 2. Dermofug Solution Combined with Either Salicylic Acid Tincture or Phenol Acid Tincture" Abstract, Database Biosis, Zentralblatt für Bakteriologie, Mikrobiologie und Hygiene vol. 186, No. 5-6; 1988; 1 page.

(Continued)

*Primary Examiner* — Gina C Justice
(74) *Attorney, Agent, or Firm* — Hovey Williams LLP

(57) ABSTRACT

Long-lasting persistent, uniform, film-forming skin protecting compositions provide long-lasting persistent barrier films when applied to skin. The compositions have particular utility as barrier teat dips for protecting cows against mastitis and as wound care agents. A barrier film-forming agent is selected from pullulan, pullulan derivatives and combinations thereof. The barrier film-forming agent is stably solubilized in a solvent that dries to form the long-lasting, persistent, uniform film over the animal skin. The compositions may contain additives, such as antimicrobial agents that kill microorganisms.

29 Claims, 1 Drawing Sheet

(56) References Cited

FOREIGN PATENT DOCUMENTS

| WO | WO 01/13727 A1 | 3/2001 |
|---|---|---|
| WO | WO 01/41573 A1 | 6/2001 |
| WO | WO 01/57174 A1 | 8/2001 |
| WO | WO 02/34045 A1 | 5/2002 |
| WO | WO 02/059244 A2 | 8/2002 |
| WO | WO 02/065838 A1 | 8/2002 |
| WO | WO 03/003832 A1 | 1/2003 |
| WO | WO 2004/019683 A2 | 3/2004 |
| WO | WO 2007/050700 | 5/2007 |

OTHER PUBLICATIONS

Database Biosis, Hartmann, A.A., et al; "Antibacterial Efficacy of Fabry's Tinctura ono the Resident Flora of the Skin at the Forehead Study of Bacterial Population Dynamics in Stratum Corneum and Infundibulum After Single and Repeated Applications" Abstract, Database Biosis,Zentralblatt für Bakteriologie, Mikrobiologie und Hygiene; vol. 182, No. 5-6; 1986; 1 page.

Database Biosis, Liewen, M.B. & Marth, E.H; Lactic-Acid Production in Milk Containing Cleaning or Sanitizing Compounds; Abstract, Database Biosis; Journal of Food Protection, vol. 47 No. 3, 1984, 1 page.

Erskine, R.J. et al.; "Efficacy of Postmilking Disinfection with Benzyl Alcohol Versus Iodophor in the Prevention of New Intramammary Infections in Lactating Cows"; J. Dairy Sci. 81:116-120; 1998.

PCT/US2006/028768 International Search Report, Jan. 26, 2007, 10 pages.

PCT/US2006/028768 International Preliminary Report on Patentability, Jan. 29, 2008, 7 pages.

PCT/US2007/067677 International Search Report, Nov. 26, 2007, 3 pages.

PCT/US2007/069677 International Preliminary Report on Patentability, Nov. 28, 2008, 7 pages.

U.S. Appl. No. 11/192,571, 80 pages.

* cited by examiner

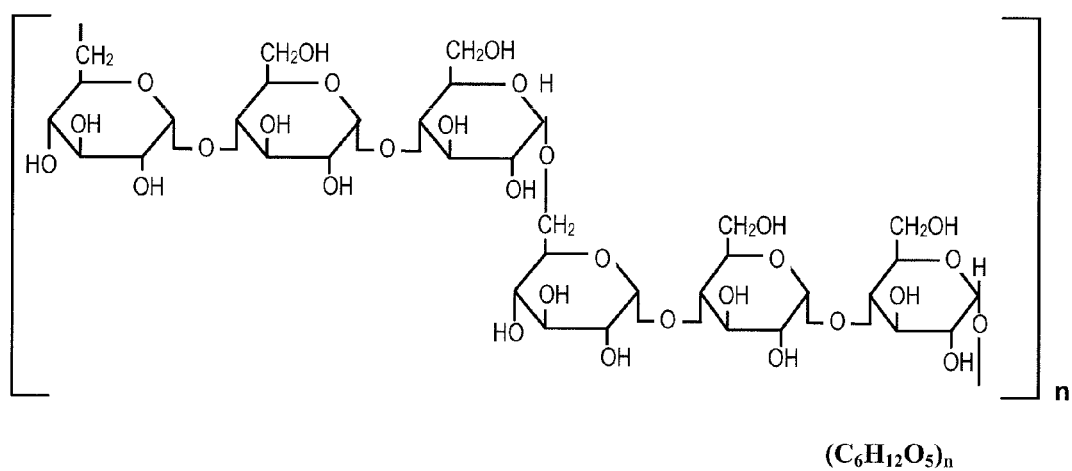
$(C_6H_{12}O_5)_n$

BARRIER FILM-FORMING COMPOSITIONS AND METHODS OF USE

RELATED APPLICATIONS

This application is a continuation-in-part application of U.S. patent application Ser. No. 11/192,571 filed on Jul. 29, 2005 now abandoned. This application is also a continuation-in-part of U.S. patent application Ser. No. 11/439,941 filed on May 24, 2006now U.S. Pat. No. 8,153,613. All of the above-identified applications are incorporated herein by reference in their entireties.

BACKGROUND

1. Field of the Invention

The present invention relates to compositions and methods for forming films that are useful, for example, in controlling mastitis and healing wounds. More particularly, pullulan-based compositions form barrier films that are useful in protecting animals from microbial infections.

2. Description of the Related Art

One major cause of economic loss for dairy farmers is the incidence of mastitis in cows and other dairy animals. Mastitis is typically caused by infection of the milk ducts by microorganisms. Severe cases of mastitis may cause death, while milder cases may result in loss of milk production together with an increased cost of veterinary care. Annual economic losses due to mastitis approximate $185 per dairy animal, which totals to approximately $1.7 billion annually for the entire United States market.

Dairy farmers have traditionally taken two approaches to prevent cows from contracting mastitis. One measure employs germicidal agents that kill microbes. The other approach uses a persistent film-forming composition that is applied to bovine teats as a barrier to block microbes from entering the milk ducts.

Despite intensive research and testing of compositions that can effectively protect animals from mastitis, many problems persist. For example, although many compositions are capable of forming a layer of film over the teat skin, some films tends to crack during drying, leaving some areas of teat skin unprotected. Other compositions form a layer of film over the skin that is too easily washed off when in contact with manure, mud or water. Still other materials cannot be removed easily enough, and may be a source of contamination that complicates the milking and milk purification processes. Moreover, some film-forming components are incompatible with germicides and other chemical ingredients that may be found in teat dip formulations, resulting in reduced potency of the germicide(s). It is difficult to formulate a protective film that is continuous, uniform, non-brittle, and persistent for 8-12 hours between milking, and mild on skin, easily removed by cleaning prior to milking, and does not drip when applied.

One type of barrier utilizes cellulose as a barrier-forming agent. For example, U.S. Pat. No. 5,776,479 issued to Pallos et al. discloses a germicidal teat dip composition that contains a film-forming ingredient selected from hydroxyethyl cellulose, methylhydroxypropyl cellulose and ethylhydroxyethyl cellulose. The composition includes a germicidal agent, such as iodine, which complexes with a nonionic surfactant and water to provide a solution having a viscosity of from about 50 to 1000 cP. After being applied to the teats of agricultural animals, the liquid dries to form a continuous barrier film.

EP 896,521 B1 describes a barrier-forming mixture that uses a long chain polysaccharide derivative, such as methyl cellulose or hydroxyethyl cellulose, which is present in an amount ranging from 10% to 20% of the composition by weight. The efficacy of this polysaccharide material is enhanced by the use of a low molecular weight saccharide material that may be, for example, a monosaccharide or disaccharide and may include hydrolyzed starches, such as maltodextrin. Although the polysaccharide material and the saccharide material are not exceptionally effective alone, a synergistic effect is achieved when the materials are used in combination such that the low molecular weight saccharide is present in an amount ranging from 2% to 10% of the composition by weight.

The use of polysaccharide-based cellulose and cellulose derivatives in teat dip compositions presents a number of problems. For example, the solutions tend to drip after application resulting in a certain amount of wasted product. Dripping of the applied solutions also results in a thinner barrier film than is ideal for use on the animals. Further, it is difficult to formulate quick-drying compositions because cellulose is relatively insoluble in commonly used volatile solvents, such as short chain alcohols.

SUMMARY

The present instrumentalities overcome the problems outlined above and advance the art by providing pullulan-based compositions that are capable of forming long-lasting, persistent, continuous, uniform films. The compositions have particular utility as barrier teat dips that may be used prophylactically against mastitis but may also be used, for example, for treating mastitis or as wound care agents. In addition to pullulan or pullulan derivative, the disclosed composition preferably contain other ingredients, which, when combined together with pullulan or pullulan derivative, are capable of forming a barrier film on the surface of a human or an animal body.

Films for protecting an animal from teat infection are preferably easily removable so as not to contaminate milk. On the other hand, the films should last long enough to protect the animal against bacterial infection between milking. The duration of film coverage is preferably 8 to 12 hours, and in some instances 24 hours or longer. Thus, a composition with too high a concentration of film forming agent may form a film that is too difficult to remove. Conversely, a composition with too low a concentration of film forming agent may form a film that is too easy to remove and does not provide sufficient protection for the animal. In one embodiment, a composition capable of forming a long-lasting, persistent barrier film includes 0.01%-20% (w/w) pullulan or pullulan derivative as a film-forming agent, wherein the pH of the composition is less than 10.

In another embodiment, a method for preventing or treating infection or for treating an animal's skin to provide a long-lasting, persistent protective barrier film includes coating the skin with a film-forming product disclosed herein, and allowing the film-forming product to dry and form a layer of film on the skin. The film-forming product may include 0.01%-10% (w/w) pullulan or pullulan derivative as a film-forming agent, wherein the pH of the composition is less than 10. In another aspect, the pH of the composition is between 3 and 7, and more preferably between 3 and 5.

In another embodiment, a method for treating or preventing mastitis comprises causing the skin of a subject in need of a prophylactic treatment to be in contact with a film-forming product disclosed herein. Suitable film-forming product may include, for example, 0.01%-5% (w/w), pullulan or pullulan derivative as a film-forming agent, wherein the pH of the composition is less than 10. The methods may further include a step to determine whether a subject is in need of a prophylactic treatment for mastitis or a step to identify a subject that is in need of such a treatment.

In a preferred embodiment, the film-forming product may contain pullulan or pullulan derivative at a concentration of 0.02%-5% (w/w), or more preferably 0.04%-3% (w/w). In another aspect, the pH of the composition to be applied to the skin of an animal is between 2 and 7, and more preferably between 2 and 5. In one particular embodiment, the pH of the composition is between 2 and 4, or more preferably between 3 and 4.

Pullulan derivatives suitable for the purpose of this disclosure may include but are not limited to one or more of the following: crosslinked pullulan, carboxy pullulan, carboxymethyl pullulan, sulfonated pullulan, sulfated pullulan, sulfopropyl pullulan, pullulan esters, diethylaminoethyl pullulan and acetylated pullulan.

The composition suitable for forming a protective film may also include at least one surfactant in the amount of between 0.01% and 10% by weight, or more preferably, in the amount of 0.05%-5% by weight. Surfactants suitable for the disclosed composition may include but are not limited to one or more of the following: alkyl sulfonic acids, alkyl sulfonate salts, aryl sulfonic acids, aryl sulfonate salts, alkylaryl sulfonic acids, alkylaryl sulfonate salts, linear alkylbenzene sulfonic acids, linear alkylbenzene sulfonate salts, alkyl α-sulfomethyl esters, alkyl α-sulfomethyl acids, alkyl α-sulfomethyl acid salts, α-olefin sulfonic acids, α-olefin sulfonate salts, alcohol ether sulfate salts, alkyl sulfate salts, alkyl ether sulfate salts, aryl ether sulfonate salts, alkylsulfo succinate salts, dialkylsulfo succinate salts, alkyl polyglucosides, alkyl ethoxylated alcohols, alkyl propoxylated alcohols, alkyl ethoxylated propoxylated alcohols, aryl ethoxylated alcohols, aryl propoxylated alcohols, arylethoxylatedpropoxylated alcohols, ethyleneoxide-propyleneoxide block copolymers, sorbitan, sorbitan esters, alkanols, alkyl betaines and alkyl amphoacetates.

The film forming composition of the present disclosure may optionally include one or more of the following components: an additional film forming agent other than pullulan or its derivatives, an antimicrobial agent, a buffering agent, a pH adjusting agent, an emollient, a humectant, a preservative, a surfactant or wetting agent, a viscosity control agent, a colorant, an opacifying agent, a skin conditioning agent, and any combinations thereof. In one aspect, the composition may contain about 0.1% to about 20% by weight of at least one antimicrobial agent.

In a preferred embodiment, the composition of the present disclosure contains pullulan and/or its derivatives as a primary film forming agent, and is substantially free from other film-forming agents other than pullulan or pullan derivatives.

The film formed on the skin of an animal may be tested for its durability. Preferably, the composition of this disclosure is capable of forming a barrier film on the surface of the teat of an animal and is capable of forming durable long term persistent barrier, yet capable of easy removal during the pre-milking preparation with dry and/or wet substrates such as a towel or by extensive washing. The barrier film is preferably sufficiently persistent when it becomes dry. Ideally, less than 70% of the barrier film is dissolved and removed from the surface of the teat after exposure to water for one minute in a solubility test ("one minute test"). More preferably, less than 50% of said barrier film is dissolved and removed from the surface of the teat after exposure to water for one minute in a solubility test.

In another aspect, the disclosed method is used for treating or preventing mastitis in a mammal such as a cow. More particularly, the method may include causing the skin of a cow in need of a prophylactic treatment to be in contact with a film-forming product disclosed herein. In one aspect, the film-forming product is applied topically to the skin of the cow's teats. In another aspect, the method may include a step for determining whether the mammal is in need of such a prophylactic treatment. For example, assays may be done on the animal(s) to determine if a particular illness is caused by infections and if so, whether a barrier protection would be effective against such infections.

BRIEF DESCRIPTION OF THE DRAWING

FIG. 1 shows the basic chemical structure of pullulan.

DETAILED DESCRIPTION

There will now be shown and described compositions and methods that effectively protect mammals from infections, such as mastitis. The compositions may form continuous, uniform, long-lasting, persistent barrier films over an animal's skin. This barrier film protects the skin from physical exposure to microbes in the environment. The compositions may also contain antimicrobial agents that kill bacteria and other microorganisms including mastitis bacteria. The antimicrobial agent may be selected from a range of antimicrobial agents which include but are not limited to: organic acids, alcohols, chlorine dioxide, chlorine dioxide releasing agents, combination of sodium chlorite with acid activators that generates chlorine dioxide, chlorhexidiene, iodophors, quaternary ammonium compounds, hypochlorite releasing compounds (e.g. alkali hypochlorite, hypochlorous acid), oxidizing compounds (e.g. hydrogen peroxide, peracids; hypochlorite), protonated carboxylic acids (e.g. heptanoic, octanoic, nonanoic, decanoic and undecanoic acids), acid anionics (e.g. alkylaryl sulfonic acids), chlorine dioxide generated from alkali chlorite by reaction with an acid activator, and bisbiguanides such as chlorhexidine. Phenolic antibacterial agents such as 2,4,4'-trichloro-2'-hydroxydiphenylether (known commercially as triclosan and may be purchased from Ciba Specialty Chemicals as IRGASAN™ and IRGASAN DP 300™), 4-chloro-3,5-dimethyl phenol (also known as PCMX and is commercially available as NIPACIDE PX and NIPACIDE PX-P), and other traditional germicides such as formaldehyde releasing compounds such as glutaraldehyde, 2-bromo-2-nitro-1,3-propanediol (Bronopol) may also be used. If certain antimicrobial agents, such as chlorhexidiene, are used, the pH of the composition is preferably above 7. The antimicrobial agent may contain an organic acid mixed with benzyl alcohol and/or a low molecular weight aliphatic alcohol having less than five carbon atoms. The antimicrobial agent may also contain an organic acid mixed with salts of alkyl sulfates, alkyl sulfonates, aryl sulfates, aryl sulfonates and other surface active agents. These antimicrobial agents may be mixed with an inactive ingredient that is formulated according to the intended environment of use.

In one aspect, the antimicrobial composition may contain at least two antimicrobial agents. For example, organic acids, such as lactic acid and/or salicylic acid, may be combined with benzyl alcohol, or isopropyl alcohol in a pharmaceutically acceptable carrier. A pharmaceutically acceptable carrier may, for example, be water.

The inactive ingredient may include, for example, an additive selected from a buffering agent, a thickener, an emollient, a humectant, a preservative, a barrier forming agent, a surfactant or wetting agent, a viscosity control agent, a colorant, an opacifying agent, and any combinations thereof.

It is one object of the disclosed instrumentalities to provide a biocidal composition that may be used, for example, according to any purpose for antibacterial or bactericidal properties. In one embodiment, the disclosed composition may be used to form one or more protective layers on the surface of a human or animal to provide physical and/or chemical protection against infections by various germs. In a particular embodiment, the composition is intended to be used as a teat dip for animals. Preferred compositions for skin applications have a pH of about 2 to about 10 and provide a substantial reduction, e.g., greater than 99.999%, in Gram positive and Gram negative bacterial populations.

Another object is to provide a composition which, when applied, results in a wound healing effect. The composition may facilitate faster and qualitatively improved healing of wounds by decreasing the number of microorganisms in the vicinity of the wound.

Yet another object is to provide a composition which, when applied, results in a prophylactic action against mastitis.

Methods of preparing the antimicrobial compositions may involve dissolving a desired concentration of antimicrobial agents and, optionally, any desired additives in a selected pharmaceutical carrier. The solution is then mixed, for example in a mixer, to form a final antimicrobial composition. Useful concentrations are those where the percentage of each antimicrobial agent by total weight of the composition is preferably from about 0.01 to 20% by weight of the composition, and a pharmaceutical carrier may be present form 80 to 99.98% by weight. More preferably, this is from about 0.02 to 15% of each antimicrobial agent. Most preferably, this is from about 0.04 to 10% of each antimicrobial agent. Still more preferably, this is from about 0.05 to 8% of each antimicrobial agent and from about 92 to 99.95% of a pharmaceutical carrier.

As used herein, the term "subject" shall include humans and terrestrial animals. For example, the subject can be a domestic livestock species, a laboratory animal species, a zoo animal, a companion animal or a human. In a particular embodiment, "subject" refers to any lactating animal including cows, sheeps, goats and buffalos; more preferably, the subject is a cow.

The phrase "therapeutically effective amount" is intended to qualify the amount of the topical composition which will achieve the goal of decreasing microbial concentration. "Therapeutically effective" may also refer to substantial improvement in the severity of the disorder or the frequency of disease incidence as compared to animals with no treatment. "Substantial improvement" means a more than 20% improvement.

The term "topical" shall refer to any composition applied to the epidermis or skin of a subject. Topical shall also refer to compositions used as mouthwashes, or used to treat or prevent disorders in other internal surface of an organ.

The term "additive" shall mean any component that is not an antimicrobial agent or a pharmaceutical carrier. A pharmaceutical carrier is generally a bulk solvent used to dilute or solubilize the components of the composition.

The terms "teat dip" or "teat dipping" shall be interpreted broadly and in accordance with the terminology used in the art of dairy farming. Thus, the composition is not only intended for dipping of the teats but it can also be applied in other ways, such as by spraying, painting, among other methods of application to the skin.

As used herein, unless otherwise specified, the term "antimicrobial" describes a biocidal effect that may be, for example, an antibacterial, antifungal, antiviral, bacteriostatic, disinfecting or sanitizing effect. Throughout this disclosure, the terms "antimicrobial," "biocidal" and "germicidal" are used interchangeably. All of these terms are used to describe an effect of certain chemicals that may be used alone or in combination to accelerate the demise or limit the growth of microorganisms. The term microorganism, as used in this disclosure, refers to the same organisms that are commonly known as "microorganisms" in the field of microbiology. Examples of microorganisms include but are not limited to bacteria, fungi, viruses and the like.

The term "apply" or "applied" shall be interpreted broadly. Thus, the composition may be contacted with the skin of an animal by a variety of means. Such means include, but are not limited to, spraying, paint brushing, spreading, foaming, teat dipping and other ways that are found acceptable in the dairy industry.

For purpose of this disclosure, the term "film forming agent" or "barrier forming agent" means a chemical or mixture thereof which when applied to a surface forms a layer or physical barrier upon drying.

The term "substantially free" means that the component may be virtually absent from a composition. As would occur in any chemical preparation process, a small amount of contaminant may exist in the composition, but when a composition is "substantially free" of an ingredient, it shall mean that the composition contains less than about 1% of the specified ingredient.

As disclosed herein, combinations of the antimicrobial agents may include an organic acid with benzyl alcohol and/or a low molecular weight aliphatic alcohol having a carbon number less than five. In particular, lactic acid, salicylic acid, benzyl alcohol, and/or isopropyl alcohol may suffice to make effective biocidal compositions. These basic ingredients may be formulated using additional antimicrobial agents, skin conditioning agents, emollients, thickeners, barrier-forming agents, viscosity control agents, pH adjusting agents, wetting agents, opacifying agents, and carriers to make a wide variety of products.

In another embodiment, a barrier film-forming agent may be the only component of the composition which, when applied to the skin of an animal forms a long lasting physical layer of protection over the skin, thus preventing microorganisms from passing through the layer. In teat dip compositions, barrier film-forming agents may coat the teat skin and, optionally, the udder, and may also form a plug at the end of an open teat canal. Generally, barrier film-forming agents are those components of a composition that remain in contact with the skin, e.g., between milking cycles. Typical barrier agents include thick creams or emollients (made with viscosity control agents), films, polymers, latex and the like. One preferred barrier film-forming agent is pullulan or its derivatives.

The compositions disclosed herein may be used for prophylactic treatment of a dairy animal's teats to provide a long-lasting, protective barrier film that demonstrates persistence between milking, and is controllably reproducible to yield a continuous, uniform, persistent barrier. Treatment processes generally entail milking an animal, coating the teat(s) and/or udder with the composition after milking, and allowing the composition to dry and form a layer of persistent barrier film on the teat(s) and/or udder. The composition may be applied topically by painting, foaming, dipping or spraying, for example. Use of the composition is not, however, limited to use against mastitis, and the composition may be used generally to treat or protect against any infectious skin condition.

In one aspect, a composition capable of forming a long-lasting, persistent, continuous, uniform barrier film may contain from about 0.01% to about 20% by weight of modified and/or unmodified pullulan for use as a barrier agent, preferably the composition contains from about 0.01% to about 10% by weight modified and/or unmodified pullulan, more preferably the composition contains between about 0.01% to about 5% by weight modified and/or unmodified pullulan, and most preferably the composition contains between 0.02% to 0.4% by weight modified and/or unmodified pullulan.

Pullulan is a polysaccharide polymer made up primarily of α-1, 6 linked maltotriose residues. The chemical structures of pullulan are variable depending upon carbon source, the microorganism that produces it (e.g., *Aureobasidium pullulans*) and fermentation conditions. The basic structure of pullulan, $(C_6H_{12}O_5)_n$, as illustrated in FIG. 1, is a linear α-glucan, made from three glucose units linked α-1,4 into maltotriose units which are linked in an α-1,6 manner. The molecular weight of pullulan may range from a few kDa to several thousand kDa. A 1% pullulan solution typically has a pH between 5 to 7, and a 2% pullulan solution typically has an apparent viscosity (rotary viscometer, 1300 s$^{-1}$) of 2 to 3.5 cP. See generally, Rekha and Sharma, Trends Biomater. Artif. Organs., Vol. 20(2), 116-121 (2007). Pullulan or pullulan derivatives can be analyzed by various methods including Gel Permeable Chromatography (GPC), High Performance Liquid Chromatography (HPLC), Thin Layer Chromatography (TLC) and also by many other methods.

Pullulan is generally soluble in water to certain extent and usually forms a stable aqueous solution that can be used to produce thermostable, transparent, elastic, antistatic films, with extremely low oxygen permeability compared to celofane, polypropylene, polyester, polyvinyl chloride, etc. Another advantage of pullulan is that it is generally considered non-toxic, edible, biodegradable and biocompatible.

products that result from chemical or biological modification of pullulan, and they may be used alone or in combination with unmodified pullulan. Pullulan derivatives may include but are not limited to, for example, crosslinked pullulan, carboxylated pullulan, carboxymethyl pullulan, sulfonated pullulan, sulfated pullulan, sulfopropyl pullulan, pullulan esters, diethylaminoethyl pullulan and acetylated pullulan. Carboxylated pullulan may be prepared by oxidizing pullulan with an oxidizing agent, such as dinitrogen tetraoxide, potassium permanganate, potassium hypochorite, air, hydrogen peroxide, nitric acid, fuming nitric acid, chromic acid, chlorine, chloric acid, potassium chlorate, nitrogen dioxide, nitric acid-sodium nitrite, phosphoric acid-sodium nitrite or nitric acid-formic acid, as described, for example, in U.S. Pat. No. 4,090,016, which is incorporated by reference. When an excess of oxidizing agent (e.g., epichlorohydrin or one of those listed above) is utilized, crosslinked pullulan may be obtained. Carboxymethyl pullulan is a crosslinked pullulan treated, for example, with an acid anhydride of sodium acetate (ClAcONa) in isopropyl alcohol. Sulfopropyl pullulan is a crosslinked pullulan treated, for example, with (Cl—PrSO$_3$Na) in isopropyl alcohol. Pullulan esters, such as pullulan acetate, may be produced by the method described in U.S. Pat. No. 3,871,892, which is incorporated by reference. Pullulan derivatives are available, for example, from the National Institute for Chemical-Pharmaceutical Research and Development Bucharest, Romania or "Petru Poni" Institute of Macromolecular Chemistry—Romanian Academy, Iasi, Romania.

As shown in Table 1, one potential advantage of using derivatized pullulan is that the solubility of pullulan derivatives in polar organic solvents tends to increase with the degree of substitution by polar moieties (e.g., acetyl groups). Thus, one skilled in the art may control the solubility of the barrier agent to facilitate use with a particular solvent, e.g., a highly volatile solvent that will quickly evaporate to form a dry film.

TABLE 1

Solubility of Derivatized Pullulan*

| Solvent | D.S. < 1 | D.S. = 1 | D.S. = 1.4 | D.S. = 1.8 | D.S. = 2.2 | D.S. = 2.4 | D.S. = 2.6 | D.S. = 2.8 |
|---|---|---|---|---|---|---|---|---|
| Water | + | + | ± | − | − | − | − | − |
| Methanol | − | − | − | ± | ± | ± | ± | ± |
| Acetone | − | − | ± | + | + | + | + | + |
| DMSO | + | + | + | + | + | + | + | + |
| DMF | ± | ± | + | + | + | + | + | + |
| CHCl$_3$ | − | − | ± | + | + | + | + | + |
| THF | − | − | ± | ± | + | + | + | + |
| Ether | − | − | − | − | − | − | − | − |
| Toluene | − | − | − | ± | ± | ± | ± | ± |
| Ethyl Acetate | − | − | ± | ± | + | + | + | + |

*Note: (−) = insoluble; (±) = swells; (+) = soluble; (D.S.) = degree of substitution with acetyl groups
**Adapted from a Catalog listed on the website of the National Institute for Chemical-Pharmaceutical Research and Development, at www.ncpri.ro/pullulan/en/index.htm In one aspect, the pullulan of this disclosure may contain up to 10% maltotetrose units and α-1,3 branch linkages, and glucose polymers may account for a minimum 80% of the pullulan portion of the composition. A 1% pullulan solution typically has a pH between 5 and 7, and a 2% pullulan solution typically has an apparent viscosity (rotary viscometer, 1300 s$^{-1}$) of 2-3.5 cP. Id.

In another embodiment, a composition may contain modified pullulan, or a pullulan derivative, as a film-forming agent. Pullulan derivatives (also termed derivatized pullulan) are The present compositions exhibit excellent chemical and rheological stability, as well as a strong clinging capacity to immobilize the persistent, continuous, uniform barrier film on skin surfaces. The compositions may form non-dripping and long-lasting, persistent, continuous, uniform barrier films when applied to animal skin, thus providing physical protection against microbial infections. Further, the disclosed compositions provide long-term persistence and protection without causing dermal irritation.

Because a small amount of the barrier film may enter a milk product, it is desirable to use compositions that contain components that are generally recognized as safe for human consumption (or "GRAS") or are approved as direct or indirect food additives. In a preferred embodiment of this disclosure, the film-forming agent meets such requirements as being safe for human consumption (or "GRAS") or having been approved as direct or indirect food additives.

Preferred compositions for skin applications, e.g., teat dipping and wound care, have a pH of about 2.0 to about 10.0 and provide a substantial reduction, e.g., greater than 99% or preferably greater than 99.999%, in Gram Positive and Gram Negative bacterial populations, as compared to animals without the disclosed barrier film.

In wound healing, the compositions may be used prophylactically, to prevent infection where none exists at the time of the treatment, or for treatment of an existing infection. Use of the compositions may result in faster and qualitatively improved healing of wounds by decreasing the number of microorganisms that are able to contact the wound and/or by decreasing the viability of microorganisms that are already in contact with the wound.

The compositions may be provided as concentrates that contain ingredients in concentrations that are in excess of what is necessary to form a persistent, uniform barrier film, and may be diluted to values within the disclosed ranges suitable for the particular applicant. The dilution may be achieved by the addition of a carrier, such as water. By way of example, in some embodiments concentrated solutions may be mixed with a diluent 1×, 2×, 3×, 4×, 5× or even up to 20× or more. A preferred diluent is water and/or a low molecular weight alcohol, e.g., methanol, ethanol, isopropanol, used alone or in combination with one or more of glycol, ethylene glycol, propylene glycol and the like. In one embodiment, a composition may be sold as a solid and diluents may be added at the point of use to create a "ready to use" composition.

In another aspect, the aforementioned compositions may be supplemented by buffering agents, pH adjusting agents, emollients, preservatives, moisturizing agents, skin conditioning agents, surfactants or wetting agents, viscosity control agents, colorants, opacifying agents and combinations thereof. These may be present in any amounts provided that the addition of the supplemental agents does not interfere with the formation of a persistent, uniform barrier film on the surface of an animal's skin and does not render the film unsafe for the animal or for consumption should any part of the film goes into the food chain.

Antimicrobial Agents

Traditional antimicrobial agents are the components of a composition that destroy microorganisms or prevent or inhibit their replication. Traditional antimicrobial agents include iodophors, quaternary ammonium compounds, hypochlorite releasing compounds (e.g. alkali hypochlorite, hypochlorous acid), oxidizing compounds (e.g. hydrogen peroxide, peracids; hypochlorite), protonated carboxylic acids (e.g. heptanoic, octanoic, nonanoic, decanoic and undecanoic acids), acid anionics (e.g. alkylaryl sulfonic acids), chlorine dioxide generated from alkali chlorite by reaction with an acid activator, and bisbiguanides such as chlorhexidine. Phenolic antibacterial agents such as 2,4,4'-trichloro-2'-hydroxydiphenylether (known commercially as triclosan and may be purchased from Ciba Specialty Chemicals as IRGASAN™ and IRGASAN DP 300™), 4-chloro-3,5-dimethyl phenol (also known as PCMX and is commercially available as NIPACIDE PX and NIPACIDE PX-P), and other traditional germicides include formaldehyde releasing compounds such as glutaraldehyde, 2-bromo-2-nitro-1,3-propanediol (Bronopol) may also be used. In one aspect, antimicrobial agents such as combined organic acids and alcohol as described in U.S. patent application Ser. No. 11/192,571 may be used to replace or eliminate the need for traditional antimicrobial agents in a wide variety of applications. In another aspect, antimicrobial agents may be prepared by combining organic acids, such as lactic acid, and anionic surfactants, such as sodium octane sulfonate or sodium lauryl sulfate, as described in International Patent application No. WO 2008/031104 A2. Such non-traditional antimicrobial agents may be used to replace or eliminate the need for traditional antimicrobial agents in a wide variety of applications. In another aspect, antimicrobial compositions disclosed herein may be used in combination with these traditional antimicrobial agents, for example, to achieve an effective kill at lower concentrations of traditional antimicrobial agents. For purpose of this disclosure, antimicrobials that have relatively low toxicity are preferred.

Barrier Forming Agents

Barrier and film forming agents are those components of a teat dipping composition that remain in contact with the teat between milking cycles. Barrier and film forming agents coat the teat skin and, optionally, the udder. Barrier agents may form a plug at the end of the open teat canal. Typical barrier and film forming agents include thick creams or emollients (made with viscosity control agents), films, polymers, latex and the like. Some nonionic surfactants may help further enhance the barrier property in addition to wetting properties. Examples of such surfactants may include, without limitation, Pluronic P105 and Pluronic F 108. A latex material that provides an effective covering of the teat is described in U.S. Pat. No. 4,113,854. Suitable barrier forming agents include, for example, latex, arabinoxylanes, glucomannanes, guar gum, johannistree gums, cellulose, methyl cellulose, ethyl cellulose, hydroxyethyl cellulose, hydroxymethyl cellulose, carboxyethyl cellulose, carboxymethyl cellulose, starch, hydroxyethyl starch, hydrolyzed starch having various degree of dextrose units (DE) such as maltodextrins, gum arabic, curdlan, pullulan, pullulan derivative, dextran, polysulfonic acid, polyacryl amide, high molecular weight polyacrylate, high molecular weight cross-linked polyacrylate, carbomer, glycerol, sodium alginate, sodium alginate cross-linked with calcium salt, xanthan gum, poly(vinyl alcohol) (PVA) and poly(N-vinylpyrrolidone) (PVP). Preferred barrier-forming agents include pullulan and its derivatives, xanthan gum, carboxymethyl cellulose, starch, hydrolyzed starch of various DE units such as maltodextrins, sodium alginate, sodium alginate cross-linked with calcium salt, PVA, hydroxyethyl cellulose and PVP. The most preferred film forming agent is pullulan and its derivatives.

Viscosity Control Agents

Viscosity control agents or traditional thickeners may be added to formulate the antimicrobial applications according to an intended environment of use. In one example, it is advantageous for some formulations to have an optimized solution viscosity to impart vertical clinging of the product onto a teat. This type of viscous product, especially one having a suitable thixotropic, pseudo plastic or viscoelastic gel strength, minimizes dripping of the product to avoid wastage and is particularly advantageous in teat dip formulations. Other applications including hard surface disinfectants have a preferred dynamic viscosity ranging from about 1 cP to 300 cP. In another example, the amount of viscosity control agents may be substantially reduced or even eliminated in other formulations, such as surface or floor disinfectants where easy cleanup is desired. An intermediate or medium viscosity composition may be useful in a hand cleaner or personal care product. It is seen from these examples that the compositions may be formulated for a wide variety of applications by altering the amount of viscosity control agents.

The teat dip formulations may benefit from a preferred dynamic viscosity ranging from 50 cP to 4000 cP, more preferably from 100 cP to 3000 cP, and even more preferably from 200 cP to 2000 cP, and 200 cP to 1000 cP, 300 cP to 800 cP, and even more preferably from 300 cP to 700 cP at the time of the composition is to be applied on to the skin of an animal.

Suitable viscosity control agents or thickeners include hemicellulose, for example arabinoxylanes and glucomannanes; plant gum materials, for example guar gum and johannistree gums; cellulose and derivatives thereof, for example methyl cellulose, ethyl cellulose, hydroxypropyl cellulose, hydroxyethyl cellulose or carboxymethyl cellulose; starch and starch derivatives, for example hydroxyethyl starch or cross linked starch; microbial polysaccharides, for example xanthan gum, sea weed polysaccharides, for example sodium alginate, carrageenan, curdlan, pullulan or dextran, dextran sulfate, whey, gelatin, chitosan, chitosan derivatives, polysulfonic acids and their salts, polyacrylamide, and glycerol. Preferred viscosity controlling agents are, different types of cellulose and derivatives thereof, particularly hydroxyalkyl cellulose, methyl cellulose, and glycerol. High molecular weight (MW>1,000,000) cross-linked polyacrylic acid type thickening agents are the products sold by B.F. Goodrich/Noveon (now Luzrizol) under their Carbopol® trademark, especially Carbopol® 941, which is the most ion-insensitive of this class of polymers, and Carbopol® 940 and Carbopol® 934. The Carbopol® resins, also known as "Carbomer", are hydrophilic high molecular weight, cross-linked acrylic acid polymers having an average equivalent weight of 76. Carbopol® 941 has a molecular weight of about 1,250,000, Carbopol® 940 has a molecular weight of approximately 4,000,000 and Carbopol 934 has a molecular weight of approximately 3,000,000. The Carbopol® resins are cross-linked with polyalkenyl polyether, e.g. about 1% of a polyallyl ether of sucrose having an average of about 5.8 alkyl groups for each molecule of sucrose. Further detailed information on the Carbopol® resins is available from B.F. Goodrich/Noveon (now Luzrizol) see for example, the B.F. Goodrich catalog GC-67, Carbopol® Water Soluble Resins. Clays and modified clays such as bentonite or laponite can also be used as thickeners. Cothickeners are often added to improve the stability of the gel matrix, for example, colloidal alumina, titania or silica, fatty acids or their salts. A latex material that provides an effective covering of the teat is described in U.S. Pat. No. 4,113,854. Typical film forming ingredients include xanthan gum, carboxymethyl cellulose, sodium alginate, sodium alginate cross-linked with calcium salt, polysulfonic acids and their salts, polyacrylamide, poly (vinyl alcohol) (PVA), hydroxyethyl cellulose and poly(N-vinylpyrrolidone) (PVP).

pH Adjusting Agents

The pH value of the composition may be selectively adjusted by the addition of acidic, basic or buffering components. Generally, an acidic pH is preferred for teat dip and wound care products. Suitable acids for use as pH adjusting agents may include, for example, acetic acid, formic acid, citric acid, lactic acid, phosphoric acid, phosphorous acid, sulfamic acid, nitric acid and hydrochloric acids. Mineral acids may be used to drastically lower the pH. The pH may be raised or made more alkaline by addition of an alkaline agent such as sodium hydroxide, ammonium hydroxide, potassium hydroxide, amine compounds such monoethanolamine, diethanolamine, triethanolamine, sodium carbonate, sodium bicarbonate, magnesium oxide, magnesium hydroxide or combinations thereof. Traditional acid buffering agents such as citric acid, lactic acid and phosphoric acid may be used to maintain the pH buffer.

The pH of the disclosed composition is broadly preferred to be in the range of less than 10 for use in teat dip formulations and other formulations that are intended to contact the skin. The pH of the disclosed composition is more preferably from 3 to 9, 3-8, 3-7, and even more preferably from 3-5. These preferred ranges of pH refer to the pH of the composition to be applied to a subject. It is to be recognized that for purpose of convenience, transportation and/or storage stability, a stock composition may be provided which may have a pH different from the disclosed range, but which pH may be adjusted on site before use to fall within the disclosed pH range.

Emollients/Skin Conditioning Agents

A broadly preferred range of emollients/skin conditioning agents is from 1% to 30% by weight of the composition. For example, skin conditioning agents may include moisturizers, such as glycerin, sorbitol, propylene glycol, Laneth-5 to 100, lanolin, lanolin alcohol, alkoxylated lanolin, allantoin, D-panthenol, polyethylene glycol (PEG) 200-10,000, polyethylene glycol esters, monoglyceryl fatty alkanoate, acyl lactylates, polyquatemium-7, glycerol cocoate/laurate, PEG-7 glyceryl cocoate, stearic acid, hydrolyzed silk peptide, silk protein, guar hydroxypropyltrimonium chloride, alkyl poly glucoside/glyceryl laurate, $B_5$ provitamin, polysorbate 80 (Tween 80), shea butter and cocoa butter; sunscreen agents, such as titanium dioxide, zinc oxide, octyl methoxycinnamate (OMC), 4-methylbenzylidene camphor (4-MBC), avobenzone, oxybenzone and homosalate; and itch-relief or numbing agents, such as aloe vera, calamine, mint, menthol, camphor, antihistamines, corticosteroids, benzocaine and paroxamine HCl.

Wetting Agents or Surfactants

Wetting agents or surfactants may be included to formulate the disclosed compositions for an intended environment of use. Typical wetting agents or surfactants are used to wet the surface of application, reduce surface tension of the surface of application so that the product can penetrate easily on the surface and remove unwanted soil. The wetting agents or surfactants of the formulation increase overall detergency of the formula, solubilize or emulsify some of the organic ingredients that otherwise would not dissolve or emulsify, and facilitate penetration of active ingredients deep onto the intended surface of application, such as animal skin. Generally, surfactants may be present from about 0.01% to about 10% by weight, preferably from about 0.1% to about 10% by weight, more preferably from about 0.5% to about 9% by weight, even more preferably from about 1% to about 8%, and most preferably from about 2% to about 6% by weight of the composition.

Suitably effective surfactants may include but are not limited to anionic, cationic, nonionic, zwitterionic and amphoteric surfactants. Suitable anionic surfactants can be chosen from alkyl sulfonic acid, alkyl sulfonate salt, alkyl sulfate salt, linear alkylbenzene sulfonic acid, a linear alkylbenzene sulfonate salt, alkyl α-sulfomethyl ester, alkyl α-olefin sulfonate salt, alcohol ether sulfate salt, alkyl sulfate salt, alkylsulfosuccinate salt, a dialkylsulfosuccinate salt, and their alkali metal, alkaline earth metal, amine and ammonium salts thereof. Specific examples are linear $C_{10}$-$C_{16}$ alkylbenzene sulfonic acid, linear $C_{10}$-$C_{16}$ alkylbenzene sulfonate or alkali metal, alkaline earth metal, amine, alkanol amine and ammonium salts thereof, e.g., sodium dodecylbenzene sulfonate, sodium octane sulfonate, sodium lauryl sulfate, sodium $C_{14}$-$C_{16}$ α-olefin sulfonate, $C_{12}$-$C_{18}$ sodium methyl α-sulfomethyl ester and $C_{12}$-$C_{18}$ disodium methyl α-sulfo fatty acid salt. Suitable nonionic surfactants can be chosen from alkyl polyglucoside, alkyl ethoxylated alcohol, alkyl propoxylated alcohol, ethoxylated propoxylated alcohol, sorbitan, sorbitan ester and alkanol amide. Specific examples include $C_8$-$C_{16}$ alkyl polyglucoside with a degree of polymerization ranging from 1 to 3, e.g., $C_8$-$C_{10}$ alkyl polyglucoside with a degree of polymerization of 1.5 (Glucopon® 200), $C_8$-$C_{16}$ alkyl polyglucoside with a degree of polymerization of 1.45 (Glucopon® 425), $C_{12}$-$C_{16}$ alkyl polyglucoside with a degree of polymerization of 1.6 (Glucopon® 625), and polyethoxylated polyoxypropylene block copolymers (poloxamers) including by way of example the Pluronice poloxamers commercialized by BASF Chemical Co. Amphoteric surfactants can be chosen from alkyl betaines, alkylamido betaines, alkylamidoalkyl betaines and alkyl amphoacetates. Suitable betaines include cocoamidopropyl betaine, and suitable amphoacetates include sodium cocoamphoacetate, sodium lauroamphoacetate and sodium cocoamphodiacetate.

Opacifying Agents and Dyes

An opacifying agent or dye is optionally included in the formulations from about 0.001% to about 5.00% by weight. Color on the skin may serve as an indicator that a particular area has been treated. To preclude any problems with possible contamination of milk, it is preferred that only FD&C Certified (food grade) dyes be used. There are many FD&C dyes available and can be used in the teat dip compositions, e.g., FD&C Red #40, FD&C Yellow #6, FD&C Yellow #5, FD&C Green #3 and FD&C Blue #1 and combinations thereof. D&C Orange #4 can also be used either alone or in combination with other dyes. Titanium dioxide ($TiO_2$) is widely used as an opacifier and can also be used in combination with various colorants.

Preservatives

Some known teat dips and wound care agents include ethylenediaminetetraacetic acid (EDTA) and/or its alkali salts which act as chelating agents to remove metal ions from hard water. The metal ions, if not removed from the composition, facilitate metalloenzyme reactions that produce energy for bacterial cell replication. Other traditional preservatives, for example, paraban, methyl paraban, ethyl paraban and glutaraldehyde may be used.

Pharmaceutical Carriers

The preferred solvent for the present compositions is water. However, one skilled in the art will recognize that solvents other than water may be used to serve the same purpose. In some embodiments, a composition may contain at least about 70% water and preferably at least about 75% water by weight based on the total weight of the formulation. Propylene glycol and ethylene glycol can also be used as a solvent either alone or in combination with water. Short chain alcohols having a carbon number less than six may be used as solvents or co-solvents to enhance the speed of drying as the composition forms a film.

EXAMPLES

The compositions and methods will be further illustrated by the following non-limiting examples, where, unless otherwise specified, ingredient amounts are reported on the basis of weight percent of the total composition.

Example 1

Film/Barrier Quality & Quantity Evaluation

The quality of continuous, uniform, persistent barrier films of the compositions was evaluated by a method described below.

Materials used were 400 mL of each product formulation to be evaluated, stainless steel panels (6×3 inches) and 600 mL beakers. The panels were washed, dried and weighed on an analytical balance. Each panel had a line drawn 2 inches from the bottom. The panels were dipped in product to the marked line and then hung to dry for four hours under ambient conditions. After four hours, the panels were weighed again and the amount of dry product that was retained on the panel was calculated as the difference between the weight after four hours and the initial weight. The film quality was visually evaluated based on whether it was dry/wet, continuous/uniform/homogeneous, discontinuous/patterned, peelable or not peelable. Further the film quality of each formulation was evaluated based on a numerical scale 1 to 5, 5 being the best with a neat, continuous, uniform, homogeneous film without having any streaks or breaks in film layer.

After the film's general appearance and weight were evaluated, the film's solubility was also tested. Panels were let to stand in 150 mL of ambient tap water for one minute. They were then dried for four hours, weighed and the amount of product that was dissolved was calculated as a percent of the total.

Example 2

Film/Barrier Residue Build-Up Evaluation

The build up of barrier or film residues over multiple uses as a simulation to actual residue build ups from barrier material on cow teats over many usages has been evaluated by a method described below.

Materials used were 400 mL of each formulation product to be evaluated, stainless steel panels (6×3 inches) and 600 mL beakers. The panels were washed, dried and weighed on an analytical balance. Each panel had a line drawn 2 inches from the bottom. The panels were dipped in product to the marked line and then hung to dry for thirty minutes. They were then dipped a second time and hung to dry for one hour. Panels were dipped a third time and hung to dry for 4.5 hours. The weight was recorded and the amount of dry film was calculated as the difference between panel with product and initial weight of the panel.

Panels with dry film were hanged overnight and then were split into three portions for film durability and solubility. One portion was dipped in 500 mL of ambient water for one minute ("one minute test"), another portion was dipped for two minutes ("two minute test") and a third portion was dipped for three minutes ("three minute test"), both also in 500 mL of ambient water. All portions were dried for four hours, weighed and the amount of product that was dissolved was calculated as a percentage of the total.

Example 3

Evaluation of Film Quality & Quantity of Pullulan Versus Traditional Film Forming Agents Table 2 shows film quality and quantity, pH, viscosity and water solubility comparisons of pullulan barrier based compositions and comparing to traditional barrier compositions including maltodextrin. All values are presented on a w/w % basis.

Use of pullulan at a barrier film agent at a concentration range between 0.1 to 1 w/w % produced film quality and quantity weights are comparable to those of conventional compositions with barriers including maltodextrin at a range between 0.5 to 3 w/w %. In Table 2, for example, maltodextrin at 2 w/w % compared to pullulan at 0.2 w/w % produced similar film weights of 0.294 grams and 0.266 grams, respectively.

TABLE 2

Comparison of Film Quality & Quantity of Pullulan versus Traditional Film Forming Agents in Teat Dip Compositions

| Ingredients | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Water | 67.87 | 70.32 | 70.22 | 70.12 | 70.02 | 69.92 | 69.82 | 69.72 | 69.62 | 69.52 | 69.42 | 69.82 | 69.32 | 68.82 | 68.32 | 69.32 | 68.32 |
| Keltrol RD[1] | 0.40 | 0.40 | 0.40 | 0.40 | 0.40 | 0.40 | 0.40 | 0.40 | 0.40 | 0.40 | 0.40 | 0.40 | 0.40 | 0.40 | 0.40 | 0.40 | 0.40 |
| Maltrin M100[2] | 3.00 | | | | | | | | | | | | | | | | |
| Pullulan | | 0.10 | 0.20 | 0.30 | 0.40 | 0.50 | 0.60 | 0.70 | 0.80 | 0.90 | 1.00 | | | | | | |
| Pure Quote B792[3] | | | | | | | | | | | | 0.50 | 1.00 | 1.50 | 2.00 | | |
| Maltrin QD M440[4] | | | | | | | | | | | | | | | | 1.00 | 2.00 |
| Allantoin[5] | 0.10 | 0.10 | 0.10 | 0.10 | 0.10 | 0.10 | 0.10 | 0.10 | 0.10 | 0.10 | 0.10 | 0.10 | 0.10 | 0.10 | 0.10 | 0.10 | 0.10 |
| FD&C Yellow # 5 | 0.024 | 0.024 | 0.024 | 0.024 | 0.024 | 0.024 | 0.024 | 0.024 | 0.024 | 0.024 | 0.024 | 0.024 | 0.024 | 0.024 | 0.024 | 0.024 | 0.024 |
| Witconate NAS-8[6] (38%) | 7.90 | 7.90 | 7.90 | 7.90 | 7.90 | 7.90 | 7.90 | 7.90 | 7.90 | 7.90 | 7.90 | 7.90 | 7.90 | 7.90 | 7.90 | 7.90 | 7.90 |
| FD&C Blue # 1 | 0.016 | 0.016 | 0.016 | 0.016 | 0.016 | 0.016 | 0.016 | 0.016 | 0.016 | 0.016 | 0.016 | 0.016 | 0.016 | 0.016 | 0.016 | 0.016 | 0.016 |
| Sorbitol[7] 70% | 14.29 | 14.29 | 14.29 | 14.29 | 14.29 | 14.29 | 14.29 | 14.29 | 14.29 | 14.29 | 14.29 | 14.29 | 14.29 | 14.29 | 14.29 | 14.29 | 14.29 |
| L-(+)-Lactic Acid[8] (88%) | 4.00 | 4.00 | 4.00 | 4.00 | 4.00 | 4.00 | 4.00 | 4.00 | 4.00 | 4.00 | 4.00 | 4.00 | 4.00 | 4.00 | 4.00 | 4.00 | 4.00 |
| Polysorbate 80[9] | 0.30 | 0.30 | 0.30 | 0.30 | 0.30 | 0.30 | 0.30 | 0.30 | 0.30 | 0.30 | 0.30 | 0.30 | 0.30 | 0.30 | 0.30 | 0.30 | 0.30 |
| Aerosol OT[10] (75%) | 0.15 | 0.15 | 0.15 | 0.15 | 0.15 | 0.15 | 0.15 | 0.15 | 0.15 | 0.15 | 0.15 | 0.15 | 0.15 | 0.15 | 0.15 | 0.15 | 0.15 |
| Pluronic F108[11] | 0.20 | 0.20 | 0.20 | 0.20 | 0.20 | 0.20 | 0.20 | 0.20 | 0.20 | 0.20 | 0.20 | 0.20 | 0.20 | 0.20 | 0.20 | 0.20 | 0.20 |
| Benzyl Alcohol | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| Sodium Hydroxide (50%) | 1.20 | 1.20 | 1.20 | 1.20 | 1.20 | 1.20 | 1.20 | 1.20 | 1.20 | 1.20 | 1.20 | 1.30 | 1.30 | 1.30 | 1.30 | 1.30 | 1.30 |
| pH, TOM[12] | 3.50 | 3.63 | 3.64 | 3.63 | 3.63 | 3.69 | 3.69 | 3.56 | 3.56 | 3.58 | 3.50 | 3.58 | 3.52 | 3.49 | 3.48 | 3.50 | 3.57 |
| Viscosity, cP, TOM[12] LV # 2 30 rpm | 523 | 560 | 523 | 555 | 595 | 635 | 605 | 671 | 646 | 612 | 615 | 558 | 571 | 57 | 535 | 665 | 574 |
| Dry Film (gm) | 0.341 | 0.257 | 0.266 | 0.264 | 0.253 | 0.283 | 0.284 | 0.245 | 0.269 | 0.294 | 0.292 | 0.288 | 0.252 | 0.258 | 0.21 | 0.274 | 0.294 |
| Film Evaluation | dry | dry | dry | dry | dry | dry | dry | dry | dry | dry | dry | dry | Dry | dry | dry | dry | dry |
| Percent Film dissolved in water | 84.0 | 89.4 | 87.3 | 86.4 | 87.2 | 84.0 | 83.9 | 84.2 | 83.4 | 85.3 | 85.5 | 88.4 | 86.2 | 89.0 | 89.7 | 89.7 | 88.6 |

[1] Xanthan gum
[2] Maltodextrin with 9-12 dextrose units
[3] Modified corn starch
[4] Quickly dispersible maltodextrin 4-7 dextrose units
[5] (2,5-Dioxo-4-imidazolidinyl)-urea
[6] Sodium octane sulfonate
[7] Hexane-1,2,3,4,5,6-hexaol
[8] L (+)-2-hydroxypropanoic acid
[9] Polyoxyethylene (20) sorbitan monooleate
[10] Sodium diocylsulfosuccinate
[11] Polyoxyethylene-polyoxypropylene glycol
[12] TOM: Time of Manufacture Example 4

Evaluation of Film Quality & Quantity of Pullulan And Traditional Film Forming Agents Table 3 shows a comparison of the film properties of pullulan and other traditional film forming agents. All values are presented on a w/w % basis.

To evaluate film accumulation or build up the same procedure as described in Example 2 was used., The panels with the barrier film were prepared as before by immersing in a composition. Three consecutive times to build the residue as described before. The panels were weighed and compared to their pre-immersion weights to determine film accumulation. Triplicate samples of each film composition were performed to investigate water solubility by submerging the panels in cold distilled water for one minute, two minutes or three minutes.

Table 3 shows that after one minute of exposure to water only 50% of a composition containing 0.3% pullulan was removed, whereas 70% of a composition containing 3% maltodextrin was removed. However, the pullulan composition was not excessively difficult to remove. Both compositions were easily removed after three minutes of exposure to water.

TABLE 3

Comparison of Film Quality of Pullulan-Based and Hydrolyzed Starch Based Compositions

| Ingredients | 1 | 2 | 3 | 4 | 5 | 6 | 7 |
|---|---|---|---|---|---|---|---|
| Water | 70.33 | 70.23 | 70.13 | 69.93 | 67.43 | 66.43 | 67.43 |
| Keltrol RD[1] | 0.40 | 0.40 | 0.40 | 0.40 | 0.40 | 0.40 | 0.40 |
| Maltrin M040[2] | | | | | | 4.00 | |
| Maltrin M100[3] | | | | | 3.00 | | 3.00 |
| Pure Quote B792[4] | | | | 0.50 | | | |
| Pullulan | 0.10 | 0.20 | 0.30 | | | | |
| Allantoin[5] | 0.10 | 0.10 | 0.10 | 0.10 | 0.10 | 0.10 | 0.10 |
| FD&C Yellow # 5 | 0.018 | 0.018 | 0.018 | 0.018 | 0.018 | 0.018 | 0.018 |
| Witconate NAS-8[6] (38%) | 7.90 | 7.90 | 7.90 | 7.90 | 7.90 | 7.90 | 7.90 |
| FD&C Blue # 1 | 0.012 | 0.012 | 0.012 | 0.012 | 0.012 | 0.012 | 0.012 |
| Sorbitol[7] (70%) | 14.29 | 14.29 | 14.29 | 14.29 | 14.29 | 14.29 | 14.29 |
| L-(+)-Lactic Acid[8] (88%) | 4.00 | 4.00 | 4.00 | 4.00 | 4.00 | 4.00 | 4.00 |
| Polysorbate 80[9] | 0.30 | 0.30 | 0.30 | 0.30 | 0.30 | 0.30 | 0.30 |
| Aerosol OT 75[10] (75%) | 0.15 | 0.15 | 0.15 | 0.15 | 0.15 | 0.15 | 0.15 |

TABLE 3-continued

Comparison of Film Quality of Pullulan-Based and Hydrolyzed Starch Based Compositions

| Ingredients | 1 | 2 | 3 | 4 | 5 | 6 | 7 |
|---|---|---|---|---|---|---|---|
| Pluronic F108[11] | 0.20 | 0.20 | 0.20 | 0.20 | 0.20 | 0.20 | 0.20 |
| Benzyl Alcohol | 1.00 | 1.00 | 1.00 | 1.00 | 1.00 | 1.00 | 1.00 |
| Sodium Hydroxide (50%) | 1.20 | 1.20 | 1.20 | 1.20 | 1.20 | 1.20 | 1.20 |
| pH | 3.49 | 3.50 | 3.47 | 3.58 | 3.59 | 3.53 | 3.58 |
| Viscosity, cP, TOM[12], LV2 30 rpm | 587 | 624 | 582 | | | | |
| Dry film, stainless steel panel (gm) | 0.583 | 0.586 | 0.658 | 0.353 | 0.686 | 0.849 | 0.541 |
| 1 minute dip, % dissolved | 71.0 | 59.8 | 50.4 | 81.4 | 70.1 | 54.4 | 82.5 |
| Dry film, stainless steel panel (gm) | 0.566 | 0.572 | 0.641 | 0.341 | 0.695 | 0.590 | 0.584 |
| 2 minute dip, % dissolved | 91.5 | 88.5 | 88.9 | 91.7 | 88.3 | 90.9 | 64.1 |
| Dry film, stainless steel panel (gm) | 0.569 | 0.648 | 0.607 | 0.324 | 0.669 | 0.782 | 0.545 |
| 3 minute dip, % dissolved | 95.8 | 93.8 | 94.6 | 95 | 92.9 | 89.1 | 93.7 |

[1]Xanthan gum
[2]Maltodextrin with 4-7 dextrose units
[3]Maltodextrin with 9-12 dextrose units
[4]Quickly dispersible maltodextrin 4-7 dextrose units
[5](2,5-Dioxo-4-imidazolidinyl)-urea
[6]Sodium octane sulfonate
[7]Hexane-1,2,3,4,5,6-hexaol
[8]L(+)-2-hydroxypropanoic acid
[9]Polyoxyethylene (20) sorbitan monooleate
[10]Sodium diocylsulfosuccinate
[11]Polyoxyethylene-polyoxypropylene glycol
[12]TOM: Time of Manufacture Example 5

Evaluation of Quality of Pullulan-Based Films Versus Traditional Filming Agents

Table 4 shows film weight, pH, viscosity and water solubility comparisons of a conventional composition including maltodextrin and compositions including pullulan. All values are presented on a w/w % basis.

Table 4 shows that pullulan-based compositions containing between 1% and 5% pullulan produced dry films weighing the same or more than a composition containing 5% maltodextrin, and the pullulan compositions were less susceptible to rapid dissolution in water. The logical reasoning is that pullulan provides excellent durable and thinner monolayer film and with higher concentration of pullulan in the formulation, the film becomes more tenacious due to more monolayer film deposition on the top and the overall film becomes more durable. As a result, with short time wash (dipping in water) will remove lesser amount from higher concentration of pullulan, but all will even out when dipped much longer in water such as 2 or 3 minutes and then all variations become the same irrespective of their pullulan concentrations.

TABLE 4

Comparison of Conventional Composition and Pullulan-Based Compositions

| Ingredients | 1 | 2 | 3 | 4 | 5 | 6 | 7 |
|---|---|---|---|---|---|---|---|
| Water | 65.69 | 69.92 | 69.42 | 68.42 | 67.42 | 66.42 | 65.42 |
| Keltrol RD[1] | 0.40 | 0.40 | 0.40 | 0.40 | 0.40 | 0.40 | 0.40 |
| Maltrin M040[2] | 5.00 | | | | | | |
| Pullulan | | 0.50 | 1.00 | 2.00 | 3.00 | 4.00 | 5.00 |
| Allantoin[3] | 0.10 | 0.10 | 0.10 | 0.10 | 0.10 | 0.10 | 0.10 |
| FD&C Yellow # 5 | 0.024 | 0.024 | 0.024 | 0.024 | 0.024 | 0.024 | 0.024 |
| Witconate NAS-8[4] (38%) | 7.90 | 7.90 | 7.90 | 7.90 | 7.90 | 7.90 | 7.90 |
| FD&C Blue #1 | 0.016 | 0.016 | 0.016 | 0.016 | 0.016 | 0.016 | 0.016 |
| Sorbitol[5] (70%) | 14.29 | 14.29 | 14.29 | 14.29 | 14.29 | 14.29 | 14.29 |
| L-(+)-Lactic Acid[6] (88%) | 4.00 | 4.00 | 4.00 | 4.00 | 4.00 | 4.00 | 4.00 |
| Polysorbate 80[7] | 0.30 | 0.30 | 0.30 | 0.30 | 0.30 | 0.30 | 0.30 |
| Aerosol OT 75[8] (75%) | 0.15 | 0.15 | 0.15 | 0.15 | 0.15 | 0.15 | 0.15 |
| Pluronic F108[9] | 0.20 | 0.20 | 0.20 | 0.20 | 0.20 | 0.20 | 0.20 |
| Benzyl Alcohol | 1.00 | 1.00 | 1.00 | 1.00 | 1.00 | 1.00 | 1.00 |
| Sodium Hydroxide (50%) | 1.40 | 1.20 | 1.20 | 1.20 | 1.20 | 1.20 | 1.20 |
| pH TOM[10] | 3.50 | 3.50 | 3.50 | 3.51 | 3.49 | 3.55 | 3.57 |
| Viscosity, cP, TOM[10] LV #2 30 rpm | 667 | 558 | 580 | 640 | 683 | 853 | 940 |
| Dry film (gm) | 0.304 | 0.279 | 0.302 | 0.318 | 0.361 | 0.411 | 0.472 |
| Film Quality | dry | sticky | dry | dry, patterned | dry, patterned | dry, patterned | dry, patterned |

TABLE 4-continued

Comparison of Conventional Composition and Pullulan-Based Compositions

| Ingredients | 1 | 2 | 3 | 4 | 5 | 6 | 7 |
|---|---|---|---|---|---|---|---|
| Panel with film, 1 minute dip, % film that was dissolved | 88.2 | 84.8 | 79.6 | 82.4 | 79.1 | 68.3 | 71.0 |

[1]Xanthan gum
[2]Maltodextrin with 4-7 dextrose units
[3](2,5-Dioxo-4-imidazolidinyl)-urea
[4]Sodium octane sulfonate
[5]Hexane-1,2,3,4,5,6-hexaol
[6]L-(+)-2-hydroxypropanoic acid
[7]Polyoxyethylene (20) sorbitan monooleate
[8]Sodium diocylsulfosuccinate
[9]Polyoxyethylene-polyoxypropylene glycol
[10]TOM: Time of Manufacture

Example 6

Evaluation of Pullulan-Based Films and Conventional Films

Table 5 shows a comparison of film accumulation of conventional compositions including maltodextrin or starch and compositions including pullulan. All values are presented on a w/w % basis.

Table 5 shows that the pullulan compositions, while containing less barrier agent, produced films with comparable accumulation and dissolution properties to the convention maltodextrin and starch compositions.

TABLE 5

Comparison of Film Accumulation of Compositions with Conventional Barrier Agents and Pullulan-Based Compositions with Lesser Concentrations

| Ingredients | 1 | 2 | 3 | 4 | 5 | 6 |
|---|---|---|---|---|---|---|
| Water | 67.87 | 70.32 | 70.22 | 70.12 | 70.02 | 69.92 |
| Keltrol RD[1] | 0.40 | 0.40 | 0.40 | 0.40 | 0.40 | 0.40 |
| Maltrin M100[2] | 3.00 | | | | | |
| Pullulan | | 0.10 | 0.20 | 0.30 | 0.40 | 0.50 |
| Pure Quote B792[3] | | | | | | |
| Maltrin QD M440[4] | | | | | | |
| Allantoin[5] | 0.10 | 0.10 | 0.10 | 0.10 | 0.10 | 0.10 |
| FD&C Yellow # 5 | 0.024 | 0.024 | 0.024 | 0.024 | 0.024 | 0.024 |
| Witconate NAS-8[6] (38%) | 7.90 | 7.90 | 7.90 | 7.90 | 7.90 | 7.90 |
| FD&C Blue # 1 | 0.016 | 0.016 | 0.016 | 0.016 | 0.016 | 0.016 |
| Sorbitol[7] (70%) | 14.29 | 14.29 | 14.29 | 14.29 | 14.29 | 14.29 |
| L-(+)-Lactic Acid[8] (88%) | 4.00 | 4.00 | 4.00 | 4.00 | 4.00 | 4.00 |
| Polysorbate 80[9] | | 0.30 | 0.30 | 0.30 | 0.30 | 0.30 |
| Aerosol OT[10] (75%) | | 0.15 | 0.15 | 0.15 | 0.15 | 0.15 |
| Pluronic F108[11] | 0.20 | 0.20 | 0.20 | 0.20 | 0.20 | 0.20 |
| Benzyl Alcohol | 1.00 | 1.00 | 1.00 | 1.00 | 1.00 | 1.00 |
| Sodium Hydroxide (50%) | 1.20 | 1.20 | 1.20 | 1.20 | 1.20 | 1.20 |
| pH, TOM[12] | 3.50 | 3.63 | 3.64 | 3.63 | 3.63 | 3.69 |
| Viscosity, cP, TOM,[12] LV2 30 rpm | 523 | 560 | 523 | 555 | 595 | 635 |
| Dry film, stainless steel panel (gm) | | 0.767 | | 0.760 | 0.775 | 0.824 |
| 1 minute dip, % dissolved | | 61.9 | | 52.1 | 51.8 | 55.3 |
| Dry film, stainless steel panel (gm) | 1.037 | 0.862 | 0.838 | 0.895 | | |
| 1 minute dip, % dissolved | 42.0 | 52.6 | 51.8 | 42.1 | | |
| Dry film, stainless steel panel (gm) | 0.967 | 0.773 | 0.788 | 0.807 | | |
| 2 minute dip, % dissolved | 78.1 | 85.0 | 86.0 | 81.3 | | |
| Dry film, stainless steel panel (gm) | 0.973 | 0.824 | 0.808 | 0.800 | | |
| 3 minute dip, % dissolved | 86.0 | 91.0 | 89.6 | 89.6 | | |

| Ingredients | 7 | 8 | 9 | 10 | 11 | 12 |
|---|---|---|---|---|---|---|
| Water | 69.82 | 69.32 | 68.82 | 68.32 | 69.32 | 68.32 |
| Keltrol RD[1] | 0.40 | 0.40 | 0.40 | 0.40 | 0.40 | 0.40 |
| Maltrin M100[2] | | | | | | |
| Pullulan | | | | | | |
| Pure Quote B792[3] | 0.50 | 1.00 | 1.50 | 2.00 | | |
| Maltrin QD M440[4] | | | | | 1.00 | 2.00 |
| Allantoin[5] | 0.10 | 0.10 | 0.10 | 0.10 | 0.10 | 0.10 |

TABLE 5-continued

Comparison of Film Accumulation of Compositions with Conventional Barrier Agents and
Pullulan-Based Compositions with Lesser Concentrations

| | | | | | | |
|---|---|---|---|---|---|---|
| FD&C Yellow # 5 | 0.024 | 0.024 | 0.024 | 0.024 | 0.024 | 0.024 |
| Witconate NAS-8[6] (38%) | 7.90 | 7.90 | 7.90 | 7.90 | 7.90 | 7.90 |
| FD&C Blue # 1 | 0.016 | 0.016 | 0.016 | 0.016 | 0.016 | 0.016 |
| Sorbitol[7] (70%) | 14.29 | 14.29 | 14.29 | 14.29 | 14.29 | 14.29 |
| L-(+)-Lactic Acid[8] (88%) | 4.00 | 4.00 | 4.00 | 4.00 | 4.00 | 4.00 |
| Polysorbate 80[9] | 0.30 | 0.30 | 0.30 | 0.30 | 0.30 | 0.30 |
| Aerosol OT[10] (75%) | 0.15 | 0.15 | 0.15 | 0.15 | 0.15 | 0.15 |
| Pluronic F108[11] | 0.20 | 0.20 | 0.20 | 0.20 | 0.20 | 0.20 |
| Benzyl Alcohol | 1.00 | 1.00 | 1.00 | 1.00 | 1.00 | 1.00 |
| Sodium Hydroxide (50%) | 1.30 | 1.30 | 1.30 | 1.30 | 1.30 | 1.30 |
| pH, TOM[12] | 3.58 | 3.52 | 3.49 | 3.48 | 3.50 | 3.57 |
| Viscosity, cP, TOM,[12] LV2 30 rpm | 558 | 571 | 575 | 535 | 665 | 574 |
| Dry film, stainless steel panel (gm) | 0.827 | 0.792 | 0.708 | 0.620 | 0.812 | 0.868 |
| 1 minute dip, % dissolved | 68.4 | 49.3 | 72.6 | 72.2 | 57.5 | 45 |
| Dry film, stainless steel panel (gm) | 0.903 | | | | | |
| 1 minute dip, % dissolved | 62.2 | | | | | |
| Dry film, stainless steel panel (gm) | 0.929 | | | | | |
| 2 minute dip, % dissolved | 79.2 | | | | | |
| Dry film, stainless steel panel (gm) | 0.788 | | | | | |
| 3 minute dip, % dissolved | 92.3 | | | | | |

[1]Xanthan gum
[2]Maltodextrin with 9-12 dextrose units
[3]Modified corn starch
[4]Quickly dispersible maltodextrin 4-7 dextrose units
[5](2,5-Dioxo-4-imidazolidinyl)-urea
[6]Sodium octane sulfonate
[7]Hexane-1,2,3,4,5,6-hexaol
[8]L-(+)-2-hydroxypropanoic acid
[9]Polyoxyethylene (20) sorbitan monooleate
[10]Sodium diocylsulfosuccinate
[11]Polyoxyethylene-polyoxypropylene glycol
[12]TOM: Time of Manufacture Example 7

Comparison of Chlorine Dioxide Barrier Teat Dip Compositions with Traditional and Pullulan-Based Film Forming Agent Table 6 shows conventional compositions containing polyvinylpyrrolidone or vinylpyrrolidone-vinylacetate copolymers compared to compositions containing pullulan. The compositions were based on a two part system containing 1:1 w/w mixtures of a base and an activator. All concentrations are expressed on a percent by weight basis.

The pullulan-based compositions had comparable viscosity, film-forming properties and film ratings, while containing about half as much pullulan as the polymer in the conventional compositions.

TABLE 6

Comparison of Conventional Barrier Teat Dip Compositions and Chlorine
Dioxide based Pullulan Barrier Film Compositions

| Ingredients | Chlorine Dioxide Alkaline Base 0 | Chlorine Dioxide Acid Activator 1 | Chlorine Dioxide Acid Activator 2 | Chlorine Dioxide Acid Activator 3 | Chlorine Dioxide Acid Activator 4 | Chlorine Dioxide Acid Activator 5 |
|---|---|---|---|---|---|---|
| Water | 98.70 | 71.58 | 71.58 | 72.78 | 72.48 | 65.18 |
| Xanthan Gum | | | | | | |
| Polyvinylpyrrolidone K-30 | | | 1.80 | | 1.00 | |
| Luvitec VA 64 ®[4] | | 1.80 | | | | 1.80 |
| Pullulan | | | | 0.60 | 0.20 | |
| Pluronic F108[5] | | 1.00 | 1.00 | 1.00 | 1.00 | 1.00 |
| Allantoin | | 0.20 | 0.20 | 0.20 | 0.20 | 0.20 |
| Glycerin | | 15.0 | 15.0 | 15.0 | 15.0 | |
| Sorbitol[6] (70%) | | | | | | 21.40 |
| Phosphoric Acid (75%) | | 5.33 | 5.33 | 5.33 | 5.33 | 5.33 |
| L-(+)-Lactic Acid (88%) | | 1.14 | 1.14 | 1.14 | 1.14 | 1.14 |
| Sodium Dioctylsulfosuccinate | | 0.20 | 0.20 | 0.20 | 0.20 | 0.20 |
| FD&C Yellow # 5 | | 0.30 | 0.30 | 0.30 | 0.30 | 0.30 |
| Tetraodium Ethylenediaminotetraacetate | 0.50 | | | | | |
| Sodium Chlorite (80%) | 0.70 | | | | | |
| Sodium Hydroxide (50%) | 0.10 | 2.85 | 2.85 | 2.85 | 2.85 | 2.85 |
| pH | 12 | 2.75 | 2.70 | 2.73 | 2.75 | 2.67 |

TABLE 6-continued

Comparison of Conventional Barrier Teat Dip Compositions and Chlorine Dioxide based Pullulan Barrier Film Compositions

| | | | | | |
|---|---|---|---|---|---|
| Viscosity after mixing Base & Activator(cP), Brookfield DVII + LV2 30 rpm | 340 | 352 | 356 | 356 | 294 |
| Film Quantity average (gm) | 0.131 | 0.131 | 0.124 | 0.105 | 0.103 |
| Film Quality Rating, 1-5 scale (5 best) | 3 | 3 | 3 | 3 | 4 |

| Ingredients | Chlorine Dioxide Acid Activator 6 | Chlorine Dioxide Acid Activator 7 | Chlorine Dioxide Acid Activator 8 | Chlorine Dioxide Udder gold Star[1] | Non-Chlorine Dioxide Lactic Acid Barrier Teat Dip[2] | Non-Chlorine Dioxide Blockade[3] |
|---|---|---|---|---|---|---|
| Water | 65.18 | 66.38 | 65.78 | | | |
| Xanthan Gum | | | | | | |
| Polyvinylpyrrolidone K-30 | 1.80 | | 1.00 | | | |
| Luvitec VA 64 ®[4] | | | | | | |
| Pullulan | | 0.60 | 0.20 | | | |
| Pluronic F108[5] | 1.00 | 1.00 | 1.00 | | | |
| Allantoin | 0.20 | 0.20 | 0.20 | | | |
| Glycerin | | | | | | |
| Sorbitol[6] (70%) | 21.40 | 21.40 | 21.40 | | | |
| Phosphoric Acid (75%) | 5.33 | 5.33 | 5.33 | | | |
| L-(+)-Lactic Acid (88%) | 1.14 | 1.14 | 1.14 | | | |
| Sodium Dioctylsulfosuccinate | 0.20 | 0.20 | 0.20 | | | |
| FD&C Yellow # 5 | 0.30 | 0.30 | 0.30 | | | |
| Tetraodium Ethylenediaminotetraacetate | | | | | | |
| Sodium Chlorite (80%) | | | | | | |
| Sodium Hydroxide (50%) | 2.85 | 2.85 | 2.85 | | | |
| pH | 2.67 | 2.77 | 2.74 | | | |
| Viscosity after mixing Base & Activator(cP), Brookfield DVII + LV2 30 rpm | 308 | 310 | 316 | 211 | 670 | 170 |
| Film Quantity average (gm) | 0.094 | 0.086 | 0.090 | 0.040 | 0.333 | 0.130 |
| Film Quality Rating, 1-5 scale (5 best) | 4 | 4 | 4 | 2 | 4 | 2 |

[1]Ecolab/Alcide Chlorine Dioxide Barrier commercial teat dip
[2]Experimental Barrier Teat Dip with Maltodextrin M40 Barrier Material
[3]DeLaval Iodine Barrier commercial teat Dip
[4]Vinylpyrrolidone (60%)-vinylacetate (40%) copolymer
[5]Polyoxyethylene-polyoxypropylene glycol
[6]Hexane-1,2,3,4,5,6-hexaol Example 8

Barrier Teat Dip Compositions Containing Chlorine Dioxide Germicide & Polyvinylpyrrolidine Film Forming Agent Table 7 shows traditional compositions containing chlorine dioxide. The compositions were based on a two part system containing 1:1 w/w mixtures of a base and an acid activator to generate chlorine dioxide. Traditional film forming or barrier agent polyvinylpyrrolidine (PVP) which is well known and widely used in teat dip compositions are shown for comparison and as reference.

TABLE 7

Traditional Chlorine Dioxide Barrier Compositions Containing PVP

| Ingredients | Alkaline Base 0 | Acid Activator 1 | Acid Activator 2 | Acid Activator 3 |
|---|---|---|---|---|
| Water | 98.91 | 87.65 | 87.75 | 87.85 |
| Sodium Chlorite (Vulcan)-76% Dry | 0.79 | | | |

TABLE 7-continued

Traditional Chlorine Dioxide Barrier Compositions Containing PVP

| Ingredients | Alkaline Base 0 | Acid Activator 1 | Acid Activator 2 | Acid Activator 3 |
|---|---|---|---|---|
| ETDA-Na$_4$ (Hemphene 220)[1] | 0.20 | | | |
| Keltrol Regular[2] | | 0.60 | 0.50 | 0.40 |
| Polyvinylpyrrolidone K-30 (PVP) | | 1.50 | 1.50 | 1.50 |
| Methanesulfonic Acid | | 3.50 | 3.50 | 3.50 |
| Citric Acid | | 3.50 | 3.50 | 3.50 |
| Pluronic F108[3] | | 1.00 | 1.00 | 1.00 |
| Sodium Hydroxide (50%) | 0.10 | 2.25 | 2.25 | 2.25 |

[1]Ethylenediaminetetraacetate terasodium salt
[2]Xanthan Gum
[3]Polyoxyethylene-polyoxypropylene glycol

Example 9

Barrier Teat Dip Compositions Containing Chlorine Dioxide Germicide & Pullulan Film Forming Agent Table 8 shows pullulan film-based barrier teat dip compositions containing chlorine dioxide. The compositions were based on a two part system containing 1:1 w/w mixtures of a base and an acid activator and when both mixed both for 0.5 to 1 hour, it generates a ready to use product with chlorine dioxide germicide with selected barrier or film forming agents. Chlorine dioxide in the product has been quantified by an UV-VIS spectroscopic method with absorbance measuring at 395 nm.

Formulations 3, 7 and 8 were tested for germicide efficacy against bacteria. A modified EN1656 germicide test involving 30 seconds contact time was performed at ambient temperature with 10% milk as the interfering substance. Chlorine dioxide concentrations were analyzed by the DPD Method 4500-ClO$_2$ D. as referenced in Standard Method For the Examination of Water and Wastewater, American Public Health Association, Washington, D.C., 4-45, 18$^{th}$ Edition, 1992. The initial bacterial count was $1.2 \times 10^9$ for *E. coli* and $1.4 \times 10^9$ for *Staph. aureus* experiments.

After one hour of chlorine dioxide generation time, the pH values of solution 3, 7 and 8 were 2.95, 3.00 and 3.05, respectively, and the chlorine dioxide concentrations were 35.9, 35.8 and 34.7 ppm, respectively. The initial bacteria concentration of *Staph. aureus* was reduced from initial counts by greater than 6 log (99.9999%) and the concentration of *E. coli* was reduced by greater than 5.9 log for all samples. After three hours generation time, the pH values of solutions 3, 7 and 8 were 3.04, 3.07 and 3.11, respectively, and the chlorine dioxide concentrations were 23.8, 35.1 and 27.5 ppm, respectively. The bacteria concentration of *Staph. aureus* was reduced from initial counts by greater than 6 log(99.9999%) and the concentration of *E. coli* was reduced by greater than 5.9 log for all samples taken after three hours of mixing base and activator. The germicide efficacy of all the formulations has been excellent after 1 hour to three hours after mixing in presence of pullulan film forming agent. The germicide efficacy has not been diminished with pullulan and the results are comparable to traditional film forming agent such as polyvinylpyrrolidone barrier material.

TABLE 8

Comparison of Traditional Chlorine Dioxide Barrier Teat Dip Compositions with Pullulan and Polyvinylpyrrolidone Film Agents

| Ingredients | Alkaline Base 0 | Acid Activator 1 | Acid Activator 2 | Acid Activator 3 | Acid Activator 4 | Acid Activator 5 | Acid Activator 6 |
|---|---|---|---|---|---|---|---|
| Water | 98.70 | 72.53 | 72.43 | 72.33 | 72.33 | 72.13 | 73.33 |
| Sodium Chlorite (Vulcan)-Dry (80%) | 0.70 | | | | | | |
| ETDA-Na$_4$ (Hemphene 220)[1] | 0.50 | | | | | | |
| Keltrol RD[2] | | 0.20 | 0.30 | 0.40 | 0.50 | 0.60 | 0.40 |
| Polyvinylpyrrolidone K-30 | | 1.50 | 1.50 | 1.50 | 1.50 | 1.50 | 0.50 |
| Pullulan | | | | | | | |
| Pluronic F108[3] | | 1.00 | 1.00 | 1.00 | 1.00 | 1.00 | 1.00 |
| Sodium Hydroxide (50%) | 0.10 | 2.90 | 2.90 | 2.90 | 2.90 | 2.90 | 2.90 |
| Allantoin[4] | | 0.20 | 0.20 | 0.20 | 0.20 | 0.20 | 0.20 |
| Glycerin | | 15.00 | 15.00 | 15.00 | 15.00 | 15.00 | 15.00 |
| Phosphoric Acid (75%) | | 5.33 | 5.33 | 5.33 | 5.33 | 5.33 | 5.33 |
| L-(+)-Lactic Acid (88%) | | 1.14 | 1.14 | 1.14 | 1.14 | 1.14 | 1.14 |
| Sodium Dioctylsulfosuccinate | | 0.20 | 0.20 | 0.20 | 0.20 | 0.20 | 0.20 |
| FD&C Yellow #5 | | 0.30 | 0.30 | 0.30 | 0.30 | 0.30 | 0.30 |
| pH | 12.00 | 2.62 | 2.66 | 2.62 | 2.62 | 2.66 | 2.67 |
| Viscosity, DVII Plus, LV2, Brookfield Viscosimeter, 30 rpm (cP) | | 201 | 245 | 355 | 608 | 1020 | 384 |
| Viscosity, DVII Plus, LV2, Brookfield Viscosimeter, 30 rpm (cP); after mixing base & activator | | 70 | 113 | 180 | 195 | 380 | 143 |
| Film Amount, average of 2 (gm) | | 0.060 | 0.007 | 0.014 | 0.045 | 0.099 | 0.074 |
| Film Rating, 1-5 scale (5 best) | | 3 | 3 | 3 | 3 | 3 | 3 |

TABLE 8-continued

Comparison of Traditional Chlorine Dioxide Barrier Teat Dip
Compositions with Pullulan and Polyvinylpyrrolidone Film Agents

| Ingredients | Acid Activator 7 | Acid Activator 8 | Acid Activator 9 | Acid Activator 10 | Acid Activator 11 | Acid Activator 12 | Acid Activator 13 |
|---|---|---|---|---|---|---|---|
| Water | 73.08 | 72.83 | 72.58 | 72.33 | 72.08 | 71.83 | 72.18 |
| Sodium Chlorite (Vulcan)-Dry (80%) | | | | | | | |
| ETDA-Na$_4$ (Hemphene 220)[1] | | | | | | | |
| Keltrol RD[2] | 0.40 | 0.40 | 0.40 | 0.40 | 0.40 | 0.40 | 0.60 |
| Polyvinylpyrrolidone K-30 | 0.75 | 1.00 | 1.25 | 1.50 | 1.75 | 2.00 | 1.50 |
| Pullulan | | | | | | | |
| Pluronic F108[3] | 1.00 | 1.00 | 1.00 | 1.00 | 1.00 | 1.00 | 1.00 |
| Sodium Hydroxide (50%) | 2.90 | 2.90 | 2.90 | 2.90 | 2.90 | 2.90 | 2.90 |
| Allantoin[4] | 0.20 | 0.20 | 0.20 | 0.20 | 0.20 | 0.20 | 0.20 |
| Glycerin | 15.00 | 15.00 | 15.00 | 15.00 | 15.00 | 15.00 | 15.00 |
| Phosphoric Acid (75%) | 5.33 | 5.33 | 5.33 | 5.33 | 5.33 | 5.33 | 5.33 |
| L-(+)-Lactic Acid (88%) | 1.14 | 1.14 | 1.14 | 1.14 | 1.14 | 1.14 | 1.14 |
| Sodium Dioctylsulfosuccinate | 0.20 | 0.20 | 0.20 | 0.20 | 0.20 | 0.20 | 0.20 |
| FD&C Yellow #5 | 0.30 | 0.30 | 0.30 | 0.30 | 0.30 | 0.30 | 0.30 |
| pH | 2.65 | 2.65 | 2.63 | 2.63 | 2.65 | 2.65 | 2.65 |
| Viscosity, DVII Plus, LV2, Brookfield Viscosimeter, 30 rpm (cP) | 349 | 354 | 393 | 400 | 450 | 469 | 880 |
| Viscosity, DVII Plus, LV2, Brookfield Viscosimeter, 30 rpm (cP); after mixing base & activator | 147 | 162 | 174 | 168 | 149 | 154 | 408 |
| Film Amount, average of 2 (gm) | 0.077 | 0.085 | 0.016 | 0.084 | 0.085 | 0.056 | 0.115 |
| Film Rating, 1-5 scale (5 best) | 3 | 2 | 3 | 3 | 3 | 3 | 3 |

| Ingredients | Acid Activator 14 | Acid Activator 15 | Acid Activator 16 | Acid Activator 17 | Acid Activator 18 | Acid Activator 19 | Acid Activator 20 |
|---|---|---|---|---|---|---|---|
| Water | 71.98 | 71.78 | 71.58 | 71.68 | 71.48 | 73.28 | 72.08 |
| Keltrol RD[2] | 0.80 | 1.00 | 1.20 | 0.60 | 0.80 | 1.00 | 1.20 |
| Polyvinylpyrrolidone K-30 | 1.50 | 1.50 | 1.50 | 2.00 | 2.00 | 2.00 | 2.00 |
| Pullulan | | | | | | | |
| Pluronic F108[3] | 1.00 | 1.00 | 1.00 | 1.00 | 1.00 | 1.00 | 1.00 |
| Sodium Hydroxide (50%) | 2.85 | 2.85 | 2.85 | 2.85 | 2.85 | 2.85 | 2.85 |
| Allantoin[4] | 0.20 | 0.20 | 0.20 | 0.20 | 0.20 | 0.20 | 0.20 |
| Glycerin | 15.00 | 15.00 | 15.00 | 15.00 | 15.00 | 15.00 | 15.00 |
| Phosphoric Acid (75%) | 5.33 | 5.33 | 5.33 | 5.33 | 5.33 | 5.33 | 5.33 |
| L-(+)-Lactic Acid (88%) | 1.14 | 1.14 | 1.14 | 1.14 | 1.14 | 1.14 | 1.14 |
| Sodium Dioctylsulfosuccinate | 0.20 | 0.20 | 0.20 | 0.20 | 0.20 | 0.20 | 0.20 |
| FD&C Yellow #5 | 0.30 | 0.30 | 0.30 | 0.30 | 0.30 | 0.30 | 0.30 |
| pH | 2.53 | 2.62 | 2.47 | 2.75 | 2.50 | 2.76 | |
| Viscosity, DVII Plus, # LV2, Brookfield Viscosimeter, 30 rpm (cP) | 1008 | | | 988 | 1500 | 1880[5] | 2493[5] |
| Viscosity, DVII Plus, # LV2, Brookfield Viscosimeter, 30 rpm (cP); after mixing base & activator | 448 | 793[5] | 1167[5] | 404 | 476 | 873[5] | 980[5] |
| Film Amount, average of 2 (gm) | 0.133 | 0.208 | 0.237 | 0.125 | 0.121 | 0.135 | 0.207 |
| Film Rating, 1-5 scale (5 best) | 3 | 3 | 2 | 3 | 2 | 2 | 2 |

| Ingredients | Acid Activator 21 | Acid Activator 22 | Acid Activator 23 | Acid Activator 24 | Acid Activator 25 | Acid Activator 26 |
|---|---|---|---|---|---|---|
| Water | 73.48 | 73.28 | 73.08 | 72.58 | 72.48 | 72.28 |
| Keltrol RD[2] | 0.60 | 0.60 | 0.60 | 0.60 | 0.60 | 0.60 |
| Polyvinylpyrrolidone K-30 | | | | | 1.00 | 1.00 |
| Pullulan | 0.20 | 0.40 | 0.60 | 0.10 | 0.20 | 0.40 |
| Pluronic F108[3] | 1.00 | 1.00 | 1.00 | 1.00 | 1.00 | 1.00 |
| Sodium Hydroxide (50%) | 2.85 | 2.85 | 2.85 | 2.85 | 2.85 | 2.85 |
| Allantoin[4] | 0.20 | 0.20 | 0.20 | 0.20 | 0.20 | 0.20 |
| Glycerin | 15.00 | 15.00 | 15.00 | 15.00 | 15.00 | 15.00 |
| Phosphoric Acid (75%) | 5.33 | 5.33 | 5.33 | 5.33 | 5.33 | 5.33 |
| L-(+)-Lactic Acid (88%) | 1.14 | 1.14 | 1.14 | 1.14 | 1.14 | 1.14 |
| Sodium Dioctylsulfosuccinate | 0.20 | 0.20 | 0.20 | 0.20 | 0.20 | 0.20 |
| FD&C Yellow #5 | 0.30 | 0.30 | 0.30 | 0.30 | 0.30 | 0.30 |
| pH | | | | | | |
| Viscosity, DVII Plus, # LV2, Brookfield Viscosimeter, 30 rpm (cP) | 1067[5] | 1107[5] | 1247[5] | 1047[5] | 1080[5] | 1113[5] |
| Viscosity, DVII Plus, # LV2, Brookfield Viscosimeter, 30 rpm (cP); after mixing base & activator | 360[5] | 353[5] | 380[5] | 320[5] | 346[5] | 360[5] |

TABLE 8-continued

Comparison of Traditional Chlorine Dioxide Barrier Teat Dip
Compositions with Pullulan and Polyvinylpyrrolidone Film Agents

| Film Amount, average of 2 (gm) | 0.060 | 0.043 | 0.104 | 0.035 | 0.127 | 0.057 |
|---|---|---|---|---|---|---|
| Film Rating, 1-5 scale (5 best) | 4 | 4 | 4 | 4 | 4 | 4 |

[1] Ethylenediaminetetraacetate terasodium salt
[2] Xanthan gum
[3] Polyoxyethylene-polyoxypropylene glycol
[4] (2,5-Dioxo-4-imidazolidinyl)-urea
[5] Brookfield DVII PRO, Activator, # RV4, 30 rpm

Example 10

Barrier Teat Dip Compositions Containing Chlorine Dioxide Germicide & Pullulan Film Forming Agent Table 9 shows pullulan film-based barrier teat dip compositions containing chlorine dioxide. The compositions were based on a two part system containing 1:1 w/w mixtures of a base and an acid activator and when both mixed both for 0.5 to 1 hour, it generates a ready to use product with chlorine dioxide germicide with selected barrier or film forming agents. Chlorine dioxide in the product has been quantified by an UV-VIS spectroscopic method.

Formulation 11 was tested for efficacy against bacteria. A modified EN1656 germicide test involving 30 seconds contact time was performed at ambient temperature with 10% milk as the interfering substance. Chlorine dioxide concentrations were analyzed by the DPD method. The initial bacterial count was $1.2 \times 10^9$ for $E.$ $coli$ experiments and $1.4 \times 10^9$ for $Staph.$ $aureus$ experiments.

After one hour generation time, the pH of the solution was 3.09 and the chlorine dioxide concentration was 31.7 ppm. The bacteria count of $Staph.$ $aureus$ was reduced by greater than 6 and the concentration of $E.$ $coli$ was less than 3.5. After three hours generation time, the pH of the solution was 3.13 and the chlorine dioxide concentration was 26.1 ppm. The bacteria count of $Staph.$ $aureus$ was reduced by greater than 6 and the concentration of $E.$ $coli$ was greater than 5.9.

TABLE 9

Comparison of Chlorine Dioxide Barrier Teat Dips with Traditional Barrier Agents and Pullulan

| Ingredients | Alkaline Base 0 | Acid Activator 1 | Acid Activator 2 | Acid Activator 3 | Acid Activator 4 | Acid Activator 5 | Acid Activator 6 |
|---|---|---|---|---|---|---|---|
| Water | 98.70 | 72.38 | 72.18 | 71.98 | 71.78 | 71.58 | 71.38 |
| Sodium Chlorite (Vulcan)-Dry (80%) | 0.70 | | | | | | |
| ETDA-Na$_4$ (Hemphene 220)[1] | 0.50 | | | | | | |
| Keltrol RD[2] | | 0.60 | 0.60 | 0.60 | 0.60 | 0.60 | 0.60 |
| Polyvinylpyrrolidone K-30 | | | | | | | |
| Polyvinylpyrrolidone K-90 | | 1.00 | 1.20 | 1.40 | 1.60 | 1.80 | 2.00 |
| Pullulan | | | | | | | |
| Luvitec VA 64[3] | | | | | | | |
| Pluronic F108[4] | | 1.00 | 1.00 | 1.00 | 1.00 | 1.00 | 1.00 |
| Sodium Hydroxide (50%) | 0.10 | 2.85 | 2.85 | 2.85 | 2.85 | 2.85 | 2.85 |
| Allantoin[5] | | 0.20 | 0.20 | 0.20 | 0.20 | 0.20 | 0.20 |
| Glycerin | | 15.00 | 15.00 | 15.00 | 15.00 | 15.00 | 15.00 |
| Phosphoric Acid (75%) | | 5.33 | 5.33 | 5.33 | 5.33 | 5.33 | 5.33 |
| L-(+)-Lactic Acid (88%) | | 1.14 | 1.14 | 1.14 | 1.14 | 1.14 | 1.14 |
| Sodium Dioctylsulfosuccinate | | 0.20 | 0.20 | 0.20 | 0.20 | 0.20 | 0.20 |
| FD&C Yellow #5 | | 0.30 | 0.30 | 0.30 | 0.30 | 0.30 | 0.30 |
| Viscosity, DVII Plus; LV2, Brookfield Viscosimeter, 30 rpm (cP), after Mixing | | 327 | 492 | 337 | 296 | 497 | 310 |
| Spindle # RV4, 30 rpm, cP | | 300 | 380 | 306 | 233 | 373 | 273 |
| Film Amount, average of 2 (gm) | | 0.041 | 0.030 | 0.021 | 0.041 | 0.034 | 0.085 |
| Film Rating, 5 best | | 2 | 2 | 2 | 2 | 2 | 3 |

| Ingredients | Acid Activator 7 | Acid Activator 8 | Acid Activator 9 | Acid Activator 10 | Acid Activator 11 | Acid Activator 12 | Acid Activator 13 |
|---|---|---|---|---|---|---|---|
| Water | 72.38 | 72.18 | 71.98 | 71.78 | 71.58 | 71.18 | 72.38 |
| Sodium Chlorite (Vulcan)-Dry (80%) | | | | | | | |
| ETDA-Na$_4$ (Hemphene 220)[1] | | | | | | | |
| Keltrol RD[2] | 0.60 | 0.60 | 0.60 | 0.60 | 0.60 | 0.60 | 0.60 |
| Polyvinylpyrrolidone K-30 | | | | | | | 1.0 |
| Polyvinylpyrrolidone K-90 | | | | | | | |
| Pullulan | | | | | | 0.20 | 0.40 |
| Luvitec VA 64[3] | 1.00 | 1.20 | 1.40 | 1.60 | 1.80 | | |
| Pluronic F108[4] | 1.00 | 1.00 | 1.00 | 1.00 | 1.00 | 1.00 | 1.00 |
| Sodium Hydroxide (50%) | 2.85 | 2.85 | 2.85 | 2.85 | 2.85 | 2.85 | 2.85 |
| Allantoin[5] | 0.20 | 0.20 | 0.20 | 0.20 | 0.20 | 0.20 | 0.20 |

TABLE 9-continued

Comparison of Chlorine Dioxide Barrier Teat Dips with Traditional Barrier Agents and Pullulan

| | | | | | | | |
|---|---|---|---|---|---|---|---|
| Glycerin | 15.00 | 15.00 | 15.00 | 15.00 | 15.00 | 15.00 | 15.00 |
| Phosphoric Acid (75%) | 5.33 | 5.33 | 5.33 | 5.33 | 5.33 | 5.33 | 5.33 |
| L-(+)-Lactic Acid (88%) | 1.14 | 1.14 | 1.14 | 1.14 | 1.14 | 1.14 | 1.14 |
| Sodium Dioctylsulfosuccinate | 0.20 | 0.20 | 0.20 | 0.20 | 0.20 | 0.20 | 0.20 |
| FD&C Yellow #5 | 0.30 | 0.30 | 0.30 | 0.30 | 0.30 | 0.30 | 0.30 |
| Viscosity, DVII Plus; LV2, Brookfield Viscosimeter, 30 rpm (cP), after Mixing | 365 | 334 | 342 | 212 | 326 | 307 | 333 |
| Spindle # RV4, 30 rpm, cP | 373 | 366 | 373 | 353 | 353 | 353 | 360 |
| Film Amount, average of 2 (gm) | 0.108 | 0.111 | 0.106 | 0.035 | 0.131 | 0.116 | 0.08 |
| Film Rating, 5 best | 3 | 3 | 3 | 2 | 3 | 3 | 3 |

| Ingredients | Acid Activator 14 | Acid Activator 15 | Acid Activator 16 | Acid Activator 17 | Acid Activator 18 | Acid Activator 19 | Acid Activator 20 |
|---|---|---|---|---|---|---|---|
| Water | 72.78 | 72.48 | 72.28 | 72.08 | 72.18 | 71.98 | 71.788 |
| Sodium Chlorite (Vulcan)-Dry (80%) | | | | | | | |
| ETDA-Na$_4$ (Hemphene 220)[1] | | | | | | | |
| Keltrol RD[2] | 0.60 | 0.60 | 0.60 | 0.60 | 0.60 | 0.60 | 0.60 |
| Polyvinylpyrrolidone K-30 | | 1.00 | 1.00 | 1.00 | | | |
| Pullulan | 0.60 | 0.20 | 0.40 | 0.60 | 0.20 | 0.40 | 0.60 |
| Luvitec VA 64[3] | | | | | 1.00 | 1.00 | 1.00 |
| Pluronic F108[4] | 1.00 | 1.00 | 1.00 | 1.00 | 1.00 | 1.00 | 1.00 |
| Sodium Hydroxide (50%) | 2.85 | 2.85 | 2.85 | 3.00 | 3.00 | 3.00 | 3.00 |
| Allantoin[5] | 0.20 | 0.20 | 0.20 | 0.20 | 0.20 | 0.20 | 0.20 |
| Glycerin | 15.00 | 15.00 | 15.00 | 15.00 | 15.00 | 15.00 | 15.00 |
| Sorbitol[6] (70%) | | | | | | | |
| Phosphoric Acid (75%) | 5.33 | 5.33 | 5.33 | 5.33 | 5.33 | 5.33 | 5.33 |
| L-(+)-Lactic Acid (88%) | 1.14 | 1.14 | 1.14 | 1.14 | 1.14 | 1.14 | 1.14 |
| Sodium Dioctylsulfosuccinate | 0.20 | 0.20 | 0.20 | 0.20 | 0.20 | 0.20 | 0.20 |
| FD&C Yellow #5 | 0.30 | 0.30 | 0.30 | 0.30 | 0.30 | 0.30 | 0.30 |
| Viscosity, DVII Plus; LV2, Brookfield Viscosimeter, 30 rpm (cP), after Mixing | 345 | 352 | 370 | 292 | 307 | 306 | 302 |
| Spindle # RV4, 30 rpm, cP | 366 | 360 | 420 | | | | |
| Film Amount, average of 2 (gm) | 0124 | 0.130 | 0.122 | 0.116 | 0.120 | 0.136 | 0.130 |
| Film Rating, 5 best | 3 | 3 | 3 | 3 | 3 | 3 | 3 |

| Ingredients | Acid Activator 21 | Acid Activator 22 | Acid Activator 23 | Acid Activator 24 | Acid Activator 25 | Acid Activator 26 | Acid Activator 27 |
|---|---|---|---|---|---|---|---|
| Water | 71.58 | 65.18 | 65.18 | 66.388 | 65.78 | 71.98 | 71.58 |
| Sodium Chlorite (Vulcan)-Dry (80%) | | | | | | | |
| ETDA-Na$_4$ (Hemphene 220)[1] | | | | | | | |
| Keltrol RD[2] | 0.60 | 0.60 | 0.60 | 0.60 | 0.60 | 0.60 | 0.60 |
| Polyvinylpyrrolidone K-30 | | | 1.80 | | 1.00 | 1.40 | 1.80 |
| Pullulan | 0.80 | | | 0.60 | 0.20 | | |
| Luvitec VA 64[3] | 1.00 | 1.80 | | | | | |
| Pluronic F108[4] | 1.00 | 1.00 | 1.00 | 1.00 | 1.00 | 1.00 | 1.00 |
| Sodium Hydroxide (50%) | 3.00 | 3.00 | 3.00 | 3.00 | 3.00 | 2.85 | 2.85 |
| Allantoin[5] | 0.20 | 0.20 | 0.20 | 0.20 | 0.20 | 0.20 | 0.20 |
| Glycerin | 15.00 | | | | | 15.00 | 15.00 |
| Sorbitol[6] (70%) | | 21.40 | 21.40 | 21.40 | 21.40 | | |
| Phosphoric Acid (75%) | 5.33 | 5.33 | 5.33 | 5.33 | 5.33 | 5.33 | 5.33 |
| L-(+)-Lactic Acid (88%) | 1.14 | 1.14 | 1.14 | 1.14 | 1.14 | 1.14 | 1.14 |
| Sodium Dioctylsulfosuccinate | 0.20 | 0.20 | 0.20 | 0.20 | 0.20 | 0.20 | 0.20 |
| FD&C Yellow #5 | 0.30 | 0.30 | 0.30 | 0.30 | 0.30 | 0.30 | 0.30 |
| Viscosity, DVII Plus; LV2, Brookfield Viscosimeter, 30 rpm (cP), after Mixing | 321 | 308 | 310 | 316 | 314 | 293 | 331 |
| Spindle # RV4, 30 rpm, cP | | | | | 346 | 346 | 373 |
| Film Amount, average of 2 (gm) | 0.124 | 0.109 | 0.106 | 0.107 | 0.105 | 0.056 | 0.131 |
| Film Rating, 5 best | 4 | 4 | 4 | 4 | 3 | 3 | 3 |

[1]Ethylenediaminetetraacetate terasodium salt
[2]Xanthan gum
[3]Vinylpyrrolidone (60%)-vinylacetate (40%) copolymer
[4]Polyoxyethylene-polyoxypropylene glycol
[5](2,5-Dioxo-4-imidazolidinyl)-urea
[6]Hexane-1,2,3,4,5,6-hexaol

Example 11

Comparative Germicidal Efficacy of Pullulan-Based Compositions Containing Chlorine Dioxide Table 10 shows comparative germicidal efficacy of chlorine dioxide formulation prototypes with pullulan barrier versus traditional chlorine dioxide commercial products such Uddergold 5 Star Barrier teat dips and 4XLA Non-Barrier teat dips, both are available commercially from Ecolab, St. Paul, Minn. A modified EN1656 germicide test involving 30 seconds contact time was performed at ambient temperature with 10% milk as the interfering substance. Chlorine dioxide concentrations in the teat dip were analyzed by the DPD method. The initial bacterial count was $8.4 \times 10^8$ for *E. coli* experiments and $1.5 \times 10^8$ for *Staph. aureus* experiments. The following commercial chlorine dioxide teat dip products are used to test germicide efficacy of experimental chlorine dioxide barrier teat dip prototype with pullulan film forming agent.

Uddergold 5 Star Barrier $ClO_2$ Product; Activator: 1.5% Lactic Acid+0.5% Mandelic Acid; Barrier Agents: Polyacryl amide and Polysulfonic Acid 4XLA Non-Barrier $ClO_2$ Product; Activator: 2.64% Lactic Acid; Barrier Agents: None, Non-Barrier Product Pullulan-Based $ClO_2$ Formulation Composition; Activator: 4% Phosphoric Acid, 1% Lactic Acid, 0.6% Keltrol, 1% PVP, 0.2% Pullulan, 15% Glycerin (see Formulation #13 in Table 9)

The pullulan-based barrier teat dip composition produced comparable bacterial kill results to the traditional chlorine dioxide compositions that are now available commercially in all generation times from 1 hour to 18 hours. Pullulan film agent has been stable in the composition and it did not reduce the kill efficacy compared to these commercial products.

TABLE 10

Germicidal Efficacy Comparison of Pullulan-Based Chlorine Dioxide Compositions versus Commercial Products

| Chlorine Dioxide Based Teat Dip Products | 1 Hour Generation | | 2 Hour Generation | | 4 Hour Generation | | 6 Hour Generation | | 18 Hour Generation | |
|---|---|---|---|---|---|---|---|---|---|---|
| | E. Coli | Staph. Aureus | E. Coli | Staph. Aureus | E. Coli | Staph. Aureus | E. Coli | Staph. Aureus | E. Coli | Staph. Aureus |
| Uddergold 5 Star Barrier Teat Dip | 7.9 | 1.2 | 7.9 | 1.0 | 7.9 | 3.2 | 7.9 | 1.8 | 7.9 | 1.2 |
| pH | 3.23 | 3.22 | 3.22 | 3.2 | 3.29 | 3.28 | 3.30 | 3.28 | 3.38 | 3.38 |
| $ClO_2$ (ppm) | 13 | 13 | 13 | 11 | 13 | 11 | 12 | 11 | 42 | 42 |
| 4XLA Non-Barrier Teat Dip | 7.9 | 7.2 | 7.9 | 7.2 | 7.9 | 7.2 | 7.9 | 7.2 | 2.8 | 1.1 |
| pH | 2.87 | 2.76 | 2.87 | 2.96 | 2.90 | 2.93 | 2.93 | 2.95 | 2.99 | 2.99 |
| $ClO_2$ (ppm) | 25 | 50 | 22 | 72 | 19 | 99 | 15 | 71 | 37 | 36 |
| Pullulan-Based Tea Dip Composition | 7.9 | 7.2 | 7.9 | 7.2 | 7.9 | 7.2 | 7.9 | 7.2 | 7.9 | 3.4 |
| pH | 2.99 | 2.90 | 3.01 | 2.94 | 3.04 | 2.97 | 3.04 | 3.00 | 3.16 | 3.16 |
| $ClO_2$ (ppm) | 47 | 75 | 42 | 94 | 30 | 72 | 18 | 57 | 88 | 88 |

Those skilled in the art will appreciate that the foregoing discussion teaches by way of example, and not by limitation. Insubstantial changes may be imposed upon the specific embodiments described here without departing from the scope and spirit of the invention.

We claim:

1. A composition comprising:
   02%-5% (w/w) pullulan or pullulan derivative as a film-forming agent;
   at least about 70% by weight of at least one solvent; and
   from about 0.01% to about 20% by weight of at least one antimicrobial agent,
   wherein said composition has a pH of less than 10, and is capable of forming a barrier film on the surface of a human or an animal body,
   wherein said composition when applied to animal skin reduces gram-positive and gram-negative bacterial populations on the surface of the animal skin by at least 99.999%.

2. The composition of claim 1, wherein the concentration of pullulan or pullulan derivative is about 0.04%-3% (w/w).

3. The composition of claim 1, wherein said composition has a pH between 2 and 7.

4. The composition of claim 1, wherein the pullulan derivative is selected from the group consisting of crosslinked pullulan, carboxy pullulan, carboxymethyl pullulan, sulfonated pullulan, sulfated pullulan, sulfopropyl pullulan, pullulan esters, diethylaminoethyl pullulan and acetylated pullulan.

5. The composition of claim 1, further comprising at least one surfactant in the amount of between 0.01% and 10% by weight.

6. The composition of claim 5, wherein the surfactant is present between 0.05%-5% by weight.

7. The composition of claim 5, wherein the surfactant is selected from the group consisting of anionic, cationic, nonionic, zwitterionic and amphoteric surfactants.

8. The composition of claim 5, wherein the surfactant is at least one member selected from the group consisting of alkyl sulfonic acids, alkyl sulfonate salts, aryl sulfonic acids, aryl sulfonate salts, alkylaryl sulfonic acids, alkylaryl sulfonate salts, linear alkylbenzene sulfonic acids, linear alkylbenzene sulfonate salts, alkyl αsulfomethyl esters, alkyl αsulfomethyl acids, alkyl αsulfomethyl acid salts, αolefin sulfonic acids, αolefin sulfonate salts, alcohol ether sulfate salts, alkyl sulfate salts, alkyl ether sulfate salts, aryl ether sulfonate salts, alkylsulfosuccinate salts, dialkylsulfo-succinate salts, alkyl polyglucosides, alkyl ethoxylated alcohols, alkyl propoxylated alcohols, alkyl ethoxylated propoxylated alcohols, aryl ethoxylated alcohols, aryl propoxylated alcohols, arylethoxylatedpropoxylated alcohols, ethyleneoxide-propyleneoxide block copolymers, sorbitan, sorbitan esters, alkanols, alkyl betaines, alkylamido betaines, alkylamidoalkyl betaines and alkyl amphoacetates.

9. The composition of claim 1, wherein the composition has a viscosity ranging from 50 cP to 4000cP.

10. The composition of claim 9, wherein the viscosity ranges from 100cP to 3000cP.

11. The composition of claim 10, wherein the viscosity ranges from 200cP. to 2000cP.

12. The composition of claim 1, wherein the antimicrobial agent is at least one member selected from the group consisting of iodine, iodophors, benzoic acid, chlorohexidine digluconate, chlorohexidine diacetate, lactic acid, benzyl alcohol, salicylic acid, isopropyl alcohol, lower alkanols ($C_1$-$C_4$), organic acids, alkyl carboxylic acids ($C_3$-$C_{10}$), organic peroxides, hydrogen peroxide, peracids, peroxy acids, bronopol (2-bromo-2-nitro-1,3-propanediol), polyhexamethylenebiguanide, quaternary ammonium compounds, alkali hypochorite, chlorine dioxide, hypohalous acid, alkali hypohalites, hypochlorous acid, chlorine dioxide precursors, bisbiguanides, chlorohexidine, p-chloro-m-xylenol, 2,4,4'-trichloro-2'-hydroxydiphenyl ether, acid anionics, protonated carboxylic acids, 4-chloro-3,5-dimethyl phenol, glutaraldehyde, dodecylbenzenesulfonic acid, alkyl sulfate salts, alkyl sulfonate salts, alkyl and aryl chlorosulfamates, and mixtures thereof.

13. The composition of claim 1 further comprising an additive selected from the group consisting of a buffering agent, a pH adjusting agent, an emollient, a thickening agent, a preservative, a moisturizing agent, a skin conditioning agent, a wetting agent, a viscosity control agent, an opacifying agent and combinations thereof.

14. The composition of claim 1, wherein said composition is capable of forming a barrier film on the surface of the teat of an animal, and less than 70% of said barrier film is dissolved and removed from the surface of said teat after exposure to water for one minute in a solubility test.

15. The composition of claim 1, wherein said composition is capable of forming a barrier film on the surface of the teat of an animal, and less than 50% of said barrier film is dissolved and removed from the surface of said teat after exposure to water for one minute in a solubility test.

16. The composition of claim 3, wherein the pH of the composition is between 2 and 5.

17. The composition of claim 16, wherein the pH of the composition is between 2 and 4.

18. The composition of claim 17, wherein the pH of the composition is between 3 and 4.

19. A method for treating an animal's skin to provide a long-lasting persistent protective barrier film, the method comprising the steps of:
coating the skin with a film-forming product; and
allowing the film-forming product to dry and form a layer of film on the skin,
wherein said film-forming product comprises the composition of claim 1.

20. The method of claim 19, wherein the film-forming product further comprises at least one surfactant in the amount of between 0.01% and 10% by weight.

21. The method of claim 19, wherein the film-forming product further comprises from about 0.01% to about 20% by weight of at least one thickener, surfactants, viscosity modifier, skin conditioning agents, emollients, pH adjusting agents, buffering agents, dyes, coloring agents, opacifying agents and combinations thereof.

22. The method of claim 20, wherein said film-forming product further comprises at least one additive selected from the group consisting of a viscosity modifier, a skin conditioning agent, a dye, a coloring agent, a buffering agent, a pH adjusting agent, an emollient, a preservative, a moisturizing agent, a skin conditioning agent, a wetting agent, an opacifying agent and combinations thereof.

23. The method of claim 20, wherein the said film-forming product is prepared by dilution of a concentrated composition.

24. A method for treating or preventing mastitis, comprising causing the skin of a subject in need of a prophylactic treatment to be in contact with a film-forming product, said film-forming product comprising the composition of claim 1.

25. The method of claim 24, wherein the subject is a cow.

26. The method of claim 25, wherein the composition is applied topically to the skin of the cow's teats.

27. The method of claim 24, wherein the antimicrobial agent is at least one member selected from the group consisting of iodine, iodophors, benzoic acid, chlorohexidine digluconate, chlorohexidine diacetate, lactic acid, benzyl alcohol, salicylic acid, isopropyl alcohol, lower alkanols ($C_1$-$C_4$), organic acids, alkyl carboxylic acids ($C_3$-$C_{10}$), organic peroxides, hydrogen peroxide, peracids, peroxy acids, bronopol (2-bromo-2-nitro-1,3-propanediol), polyhexamethylenebiguanide, quaternary ammonium compounds, alkali hypochorite, chlorine dioxide, hypohalous acid, alkali hypohalites, hypochlorous acid, chlorine dioxide precursors, bisbiguanides, chlorohexidine, p-chloro-m-xylenol, 2,4,4'-trichloro-2'-hydroxydiphenyl ether, acid anionics, protonated carboxylic acids, 4-chloro-3,5-dimethyl phenol, glutaraldehyde, dodecylbenzenesulfonic acid, alkyl sulfate salts, alkyl sulfonate salts, alkyl and aryl chlorosulfamates, and mixtures thereof.

28. The method of claim 24, wherein the pH of the composition is between 2 and 5.

29. A composition capable of forming a barrier film, comprising:
0.02%-5% (w/w) pullulan or pullulan derivative as a film-forming agent;
at least about 70% by weight of at least one solvent; and
from about 0.01% to about 20% by weight of at least one antimicrobial agent,
said composition having a pH of less than 7,
wherein said composition when applied to animal skin reduces gram-positive and gram-negative bacterial populations on the surface of the animal skin by at least 99.999%.

* * * * *